United States Patent [19]
Bandman et al.

[11] Patent Number: 5,837,841
[45] Date of Patent: Nov. 17, 1998

[54] HUMAN REG PROTEIN

[75] Inventors: Olga Bandman, Mountain View; Surya K. Goli, Sunnyvale, both of Calif.

[73] Assignee: Incyte Pharmaceuticals, Inc., Palo Alto, Calif.

[21] Appl. No.: 729,103

[22] Filed: Oct. 11, 1996

[51] Int. Cl.⁶ .............................. C07H 21/04; C12Q 1/68; C12P 21/06; C12N 15/00
[52] U.S. Cl. .......................... 536/23.5; 435/6; 435/69.1; 435/172.3
[58] Field of Search ................................ 536/23.5; 435/6, 435/69.1, 172.3

[56] References Cited

FOREIGN PATENT DOCUMENTS

WO 96/39541  12/1996  WIPO .

OTHER PUBLICATIONS

Barondes et al., "Galectins—Structure and Function of a Large Family of Animal Lectins," *The Journal of Biological Chemistry*, 269(33):20807–20810 (1994).
Stoolman et al., "Adhesion Molecules Controlling Lymphocyte Migration," *Cell*, 56:907–910 (Mar. 24, 1989).
Drickamer et al., "Ca2+–dependent carbohydrate–recognition domains in animal proteins," *Current Opinion in Structural Biology*, 3:393–400 (1993).
Unno et al., "Structure, Chromosomal Localization, and Expression of Mouse reg Genes, reg I and reg II," *The Journal of Biological Chemistry*, 268(21):15974–15982 (1993).
Terazono et al., "A Novel Gene Activated in Regenerating Islets," *The Journal of Biological Chemistry*, 263(5):2111–2114 (1988).
Watanabe et al., "Complete Nucleotide Sequence of Human reg Gene and Its Expression in Normal and Tumoral Tissues," *The Journal of Biological Chemistry*, 265(13):7432–7439 (1990).

Moriizumi et al., "Isolation, structural determination and expression of a novel reg gene, human reg Iβ," *Biochimica et Biophysica Acta 1217* (1994) (GI474306).
Dusetti et al., "Rapid PCR Cloning and Sequence Determination of the rat lithostathine gene," *Biochimica et Biophysica Acta.*, 1174:99–102 (1993) (GI393209).
de la Monte et al., "Enhanced Expression of an Exocrine Pancreatic Protein in Alzheimer's Disease and the Developing Human Brain," *J. Clin. Invest.*, 86:1004–1013 (1990).
Giorgi et al., "Secretory Pancreatic Stone Protein Messenger RNA," *J. Clin. Invest.*, 84:100–106 (Jul. 1989).
Rouimi et al., Cleavage of the Arg–Ile bond in the native polypeptide chain of human pancreatic stone protein, *FEBS Lett.*, 216:195 (1987).
Francis et al., "Expression of an islet regenerating (reg) gene in isolated rat islets . . . ," *Diabetologia*, 35:238–242 (1992).

(List continued on next page.)

*Primary Examiner*—Jeffrey Stucker
*Assistant Examiner*—Hankyel T. Park
*Attorney, Agent, or Firm*—Lucy J. Billings; Incyte Pharmaceuticals

[57] ABSTRACT

The present invention provides a polynucleotide (reg Iγ) which identifies and encodes a novel human Reg Iγ. The invention provides for genetically engineered expression vectors and host cells comprising the nucleic acid sequence encoding human Reg Iγ. The invention also provides for the use of purified Reg Iγ and its agonists in the production of recombinant proteins and in pharmaceutical compositions for the treatment of diseases associated with the expression of Reg Iγ. Additionally, the invention provides for the use of Reg Iγ antagonists and inhibitors, including antisense molecules to reg Iγ in pharmaceutical compositions for the treatment of diseases associated with the expression of Reg Iγ. The invention also describes diagnostic assays which utilize the polynucleotide to hybridize with the transcripts and/or genomic DNA encoding Reg Iγ and anti-human Reg Iγ antibodies which specifically bind to Reg Iγ.

11 Claims, 6 Drawing Sheets

```
              9        18        27        36        45        54
5' TGA AGA AGG CAG GGG CCC TTA GAG TCT TGG TTG CCA AAC AGA TTT GCA GAT CAA 63        72        81        90        99       108
    GGA GAA CCC AGG AGT TTC AAA GAA GCG CTA GTA AGG TCT CTG AGA TCC TTG CAC 117       126       135       144       153       162
    TAG CTA CAT CCT CAG GGT AGG AGG AAG ATG GCT TCC AGA AGC ATG CGG CTG CTC
                                          M   A   S   R   S   M   R   L   L 171       180       189       198       207       216
    CTA TTG CTG AGC TGC CTG GCC AAA ACA GGA GTC CTG GGT GAT ATC ATC ATG AGA
     L   L   L   S   C   L   A   K   T   G   V   L   G   D   I   I   M   R 225       234       243       252       261       270
    CCC AGC TGT GCT CCT GGA TGG TTT TAC CAC AAG TCC AAT TGC TAT GGT TAC TTC
     P   S   C   A   P   G   W   F   Y   H   K   S   N   C   Y   G   Y   F 279       288       297       306       315       324
    AGG AAG CTG AGG AAC TGG TCT GAT GCC GAG CTC GAG TGT CAG TCT TAC GGA AAC
     R   K   L   R   N   W   S   D   A   E   L   E   C   Q   S   Y   G   N 333       342       351       360       369       378
    GGA GCC CAC CTG GCA TCT ATC CTG AGT TTA AAG GAA GCC AGC ACC ATA GCA GAG
     G   A   H   L   A   S   I   L   S   L   K   E   A   S   T   I   A   E 387       396       405       414       423       432
    TAC ATA AGT GGC TAT CAG AGA AGC CAG CCG ATA TGG ATT GGC CTG CAC GAC CCA
     Y   I   S   G   Y   Q   R   S   Q   P   I   W   I   G   L   H   D   P 441       450       459       468       477       486
    CAG AAG AGG CAG CAG TGG CAG TGG ATT GAT GGG GCC ATG TAT CTG TAC AGA TCC
     Q   K   R   Q   Q   W   Q   W   I   D   G   A   M   Y   L   Y   R   S 495       504       513       522       531       540
    TGG TCT GGC AAG TCC ATG GGT GGG AAC AAG CAC TGT GCT GAG ATG AGC TCC AAT
     W   S   G   K   S   M   G   G   N   K   H   C   A   E   M   S   S   N 549       558       567       576       585       594
    AAC AAC TTT TTA ACT TGG AGC AGC AAC GAA TGC AAC AAG CGC CAA CAC TTC CTG
     N   N   F   L   T   W   S   S   N   E   C   N   K   R   Q   H   F   L 603       612
    TGC AAG TAC CGA CCA TAG AG 3'
     C   K   Y   R   P   *
```

OTHER PUBLICATIONS

Bernard et al., "Inhibition of Nucleation and Crystal Growth of Calcium Carbonate by Human Lithostathine," *Gastroenterology*, 103:1277–1284 (1992).

Bernard et al., "Immunoreactive Forms of Pancreatic Stone Protein in Six Mammalian Species," *Pancreas*, 6(2):162–167 (1991).

Ozturk et al., Elevated levels of an exocrine pancreatic secretory protein in Alzheimer disease brain, *Proc. Natl. Acad. Sci. USA*, 86:419.

Iovanna et al., "Messenger RNA Sequence and Expression of Rat Pancreatitis–associated Protein, a Lectin–related Protein Overexpressed during Acute Experimental Pancreatitis," *The Journal of Biological Chemistry*, 266(36):24664–24669 (1991).

Orelle, "Human Pancreatitis–associated Protein," *J. Clin. Invest.*, 90:2284–2291 (Dec.).

Itoh et al., Cloning and tissue–specific expression of cDNAs for the human and mouse homologues of . . . , *Biochem. Biophys. Acta*, 1172:184.

Dusetti et al., "Molecular Cloning, Genomic Organization, and Chromosomal Localization of the Human Pancreatitis–Associated Protein (PAP) Gene," *Genomics*, 19:108–114 (1994).

Keim et al., Characterization of a Rat Pancreatic Secretory Protein Associated with Pancreatitis, *Gastroenterology*, 100:775–782 (1991).

Christa et al., The human HIP gene, overexpressed in primary liver cancer encodes for a C–type carbohydrate binding protein with lactose binding activity . . . , *FEBS Lett.*, 337:114 (1994).

Lasserre et al., "A Novel Gene (HIP) Activated in Human Primary Liver Cancer," *Cancer Research*, 52:5089–5095 (1992).

Multigener et al., "Pancreatic Stone Protein. II. Implication in Stone Formation During the Course of Chronic Calcifying Pancreatitis," *Gastroenterology*, 89:387–391 (1985).

Gross et al., "An unusual bovine pancreatic protein exhibiting pH–dependent . . . ," *Proc. Natl. Acad. Sci. USA*, 82:5627 (1985).

Drickamer, "Two Distinct Classes of Carbohydrate–recognition Domains in Animal Lectins," *The Journal of Biological Chemistry*, 263(20):9557–9560 (Jul. 15, 1988).

Drickamer et al., "Exon Structure of a Mannose–binding Protein Gene Reflects Its Evolutionary Relationship to the Asialoglycoprotein Receptor and Nonfibrillar Collagens," *The Journal of Biological Chemistry*, 262(6):2582–2589 (1987).

Dusetti et al., "Cloning, expression and chromosomal localization of the rat pancreatitis–associated protein III gene," *Biochem J.*, 307:9–16 (1995).

Dusetti et al., "Induction of Lithostathine/reg mRNA Expression by Serum from Rats with Acute Pancreatitis and . . . " *Archives of Biochemistry and Biophysics*, 330(1):129–132 (1996).

Frigerio et al., "Identification of a Second Rat Pancreatitis–Associated Protein. Messenger RNA Cloning, Gene Structure, and Expression during Acute Pancreatitis," *Biochemistry*, 32:9236–9241 (1993).

Gharib et al., "Human regeneration protein/lithostathine genes map to chromosome 2p12," *Ann. Hum. Genet.*, 57:9–16 (1993).

Rouquier et al., Rat pancreatic stone protein messenger RNA: abundant expression in mature exocrine cells, regulation by food content, and sequence identify with the endocrine reg transcript, J. Biol. Chem. 266, 786–791, 1991.

Wilson et al., 2.2. Mb of contiguous nucleotide sequence from chromosome III of C. elegans., Nature 368 (6466), 32–38, 1994.

Database EMBL, entry HSZZ19915, Accession No. AA314779, Apr. 18, 1997, XP–00205345.

```
                    9              18             27             36             45             54
5' TGA AGA AGG CAG GGG CCC TTA GAG TCT TGG TTG CCA AAC AGA TTT GCA GAT CAA 63             72             81             90             99            108
    GGA GAA CCC AGG AGT TTC AAA GAA GCG CTA GTA AGG TCT CTG AGA TCC TTG CAC 117            126            135            144            153            162
    TAG CTA CAT CCT CAG GGT AGG AGG AAG ATG GCT TCC AGA AGC ATG CGG CTG CTC
                                                  M   A   S   R   S   M   R   L   L 171            180            189            198            207            216
    CTA TTG CTG AGC TGC CTG GCC AAA ACA GGA GTC CTG GGT GAT ATC ATC ATG AGA
    L   L   L   S   C   L   A   K   T   G   V   L   G   D   I   I   M   R 225            234            243            252            261            270
    CCC AGC TGT GCT CCT GGA TGG TTT TAC CAC AAG TCC AAT TGC TAT GGT TAC TTC
    P   S   C   A   P   G   W   F   Y   H   K   S   N   C   Y   G   Y   F 279            288            297            306            315            324
    AGG AAG CTG AGG AAC TGG TCT GAT GCC GAG CTC GAG TGT CAG TCT TAC GGA AAC
    R   K   L   R   N   W   S   D   A   E   L   E   C   Q   S   Y   G   N 333            342            351            360            369            378
    GGA GCC CAC CTG GCA TCT ATC CTG AGT TTA AAG GAA GCC AGC ACC ATA GCA GAG
    G   A   H   L   A   S   I   L   S   L   K   E   A   S   T   I   A   E 387            396            405            414            423            432
    TAC ATA AGT GGC TAT CAG AGA AGC CAG CCG ATA TGG ATT GGC CTG CAC GAC CCA
    Y   I   S   G   Y   Q   R   S   Q   P   I   W   I   G   L   H   D   P 441            450            459            468            477            486
    CAG AAG AGG CAG CAG TGG CAG TGG ATT GAT GGG GCC ATG TAT CTG TAC AGA TCC
    Q   K   R   Q   Q   W   Q   W   I   D   G   A   M   Y   L   Y   R   S 495            504            513            522            531            540
    TGG TCT GGC AAG TCC ATG GGT GGG AAC AAG CAC TGT GCT GAG ATG AGC TCC AAT
    W   S   G   K   S   M   G   G   N   K   H   C   A   E   M   S   S   N 549            558            567            576            585            594
    AAC AAC TTT TTA ACT TGG AGC AGC AAC GAA TGC AAC AAG CGC CAA CAC TTC CTG
    N   N   F   L   T   W   S   S   N   E   C   N   K   R   Q   H   F   L 603            612
    TGC AAG TAC CGA CCA TAG AG 3'
    C   K   Y   R   P   *
```

Decoration 'Decoration #1': Box residues that match the Consensus exactly.

FIGURE 2

| Library | Lib Description | Abun | Pct Abun |
|---|---|---|---|
| OVARNOT03 | ovary, 43 F, match to OVARTUT01 | 5 | 0.1932 |
| OVARTUT01 | ovarian tumor, 43 F, match to OVARNOT03 | 3 | 0.0968 |
| COLNNOT05 | colon, 40 M, match to COLNCRT01 | 2 | 0.0577 |
| PANCNOT08 | pancreas, 65 F, match to PANCTUT01 | 1 | 0.0254 |
| COLNFET02 | colon, fetal F | 1 | 0.0142 |

FIGURE 3

```
            10        20        30        40        50        60        70
       MASRSMRLLLLLSCLAKTGVLGDIIMRPSCAPGWFYHKSNCYGYFRKLRNWSDAELECQSYGNGAHLASI
HELIX        hhhhhhhhhhH                                 HHhhhhHHHh       hHhhhh
SHEET      sSSSSSSSSSsSSSSSSSSSSS       sss         sSSSS        sss         SSSS
TURN   TTTTT                      TTTTTTTT  TTTTTTTT     TTTT    TTTTTTTT
COIL   C
            80        90       100       110       120       130       140
       LSLKEASTIAEYISGYQRSQPIWIGLHDPQKRQQWQWIDGAMYLYRSWSGKSMGGNKHCAEMSSNNNFLT
HELIX  hhHHHHHhhhH         hhhhhHH   hhHHHHHHHHHHH                hhHHh
SHEET  SSs      SSSsSs        sSSSSSs   ssssssssssssssSSSSSs                sSS
TURN              TTTTTTTT       TTTT             TTTTTTTTTTTT   TTTTTTT
COIL
            150
       WSSNECNKRQHFLCKYRP
HELIX           hhhhhH
SHEET  s      sSSSSSsS
TURN   TTTTTTTTTT
COIL                 cc
```

FIGURE 6

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 158 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: COLNFET02
        ( B ) CLONE: 1310334

( x i ) SEQUENCE DESCRIPTION: SEQ ID NO:1:

```
Met Ala Ser Arg Ser Met Arg Leu Leu Leu Leu Leu Ser Cys Leu Ala
 1               5                  10                  15
Lys Thr Gly Val Leu Gly Asp Ile Ile Met Arg Pro Ser Cys Ala Pro
             20                  25                  30
Gly Trp Phe Tyr His Lys Ser Asn Cys Tyr Gly Tyr Phe Arg Lys Leu
         35                  40                  45
Arg Asn Trp Ser Asp Ala Glu Leu Glu Cys Gln Ser Tyr Gly Asn Gly
     50                  55                  60
Ala His Leu Ala Ser Ile Leu Ser Leu Lys Glu Ala Ser Thr Ile Ala
 65                  70                  75                  80
Glu Tyr Ile Ser Gly Tyr Gln Arg Ser Gln Pro Ile Trp Ile Gly Leu
                 85                  90                  95
His Asp Pro Gln Lys Arg Gln Gln Trp Gln Trp Ile Asp Gly Ala Met
             100                 105                 110
Tyr Leu Tyr Arg Ser Trp Ser Gly Lys Ser Met Gly Gly Asn Lys His
         115                 120                 125
Cys Ala Glu Met Ser Ser Asn Asn Asn Phe Leu Thr Trp Ser Ser Asn
     130                 135                 140
Glu Cys Asn Lys Arg Gln His Phe Leu Cys Lys Tyr Arg Pro
145                 150                 155
```

( 2 ) INFORMATION FOR SEQ ID NO:2:

( i ) SEQUENCE CHARACTERISTICS:
        ( A ) LENGTH: 614 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: COLNFET02
        ( B ) CLONE: 1310334

( x i ) SEQUENCE DESCRIPTION: SEQ ID NO:2:

```
TGAAGAAGGC AGGGGCCCTT AGAGTCTTGG TTGCCAAACA GATTTGCAGA TCAAGGAGAA      60
```

-continued

| | | | | | |
|---|---|---|---|---|---|
| CCCAGGAGTT | TCAAAGAAGC | GCTAGTAAGG | TCTCTGAGAT | CCTTGCACTA | GCTACATCCT | 120
| CAGGGTAGGA | GGAAGATGGC | TTCCAGAAGC | ATGCGGCTGC | TCCTATTGCT | GAGCTGCCTG | 180
| GCCAAAACAG | GAGTCCTGGG | TGATATCATC | ATGAGACCCA | GCTGTGCTCC | TGGATGGTTT | 240
| TACCACAAGT | CCAATTGCTA | TGGTTACTTC | AGGAAGCTGA | GGAACTGGTC | TGATGCCGAG | 300
| CTCGAGTGTC | AGTCTTACGG | AAACGGAGCC | CACCTGGCAT | CTATCCTGAG | TTTAAAGGAA | 360
| GCCAGCACCA | TAGCAGAGTA | CATAAGTGGC | TATCAGAGAA | GCCAGCCGAT | ATGGATTGGC | 420
| CTGCACGACC | CACAGAAGAG | GCAGCAGTGG | CAGTGGATTG | ATGGGCCAT | GTATCTGTAC | 480
| AGATCCTGGT | CTGGCAAGTC | CATGGGTGGG | AACAAGCACT | GTGCTGAGAT | GAGCTCCAAT | 540
| AACAACTTTT | TAACTTGGAG | CAGCAACGAA | TGCAACAAGC | GCCAACACTT | CCTGTGCAAG | 600
| TACCGACCAT | AGAG | | | | | 614

( 2 ) INFORMATION FOR SEQ ID NO:3:

( i ) SEQUENCE CHARACTERISTICS:
        ( A ) LENGTH: 165 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 393209

( x i ) SEQUENCE DESCRIPTION: SEQ ID NO:3:

```
Met  Thr  Arg  Asn  Lys  Tyr  Phe  Ile  Leu  Leu  Ser  Cys  Leu  Met  Val  Leu
 1              5                        10                       15

Ser  Pro  Ser  Gln  Gly  Gln  Glu  Ala  Glu  Asp  Leu  Pro  Ser  Ala  Arg
            20                  25                      30

Ile  Thr  Cys  Pro  Glu  Gly  Ser  Asn  Ala  Tyr  Ser  Ser  Tyr  Cys  Tyr  Tyr
            35                       40                       45

Phe  Met  Glu  Asp  His  Leu  Ser  Trp  Ala  Glu  Ala  Asp  Leu  Phe  Cys  Gln
      50                       55                       60

Asn  Met  Asn  Ser  Gly  Tyr  Leu  Val  Ser  Val  Leu  Ser  Gln  Ala  Glu  Gly
65                       70                       75                       80

Asn  Phe  Leu  Ala  Ser  Leu  Ile  Lys  Glu  Ser  Gly  Thr  Thr  Ala  Ala  Asn
                      85                       90                       95

Val  Trp  Ile  Gly  Leu  His  Asp  Pro  Lys  Asn  Asn  Arg  Arg  Trp  His  Trp
                 100                      105                      110

Ser  Ser  Gly  Ser  Leu  Phe  Leu  Tyr  Lys  Ser  Trp  Asp  Thr  Gly  Tyr  Pro
            115                      120                      125

Asn  Asn  Ser  Asn  Arg  Gly  Tyr  Cys  Val  Ser  Val  Thr  Ser  Asn  Ser  Gly
      130                      135                      140

Tyr  Lys  Lys  Trp  Arg  Asp  Asn  Ser  Cys  Asp  Ala  Gln  Leu  Ser  Phe  Val
145                      150                      155                      160

Cys  Lys  Phe  Lys  Ala
                 165
```

( 2 ) INFORMATION FOR SEQ ID NO:4:

( i ) SEQUENCE CHARACTERISTICS:
        ( A ) LENGTH: 166 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
    ( A ) LIBRARY: GenBank
    ( B ) CLONE: 474306

( x i ) SEQUENCE DESCRIPTION: SEQ ID NO:4:

```
Met Ala Gln Thr Asn Ser Phe Phe Met Leu Ile Ser Ser Leu Met Phe
 1               5                  10                  15
Leu Ser Leu Ser Gln Gly Gln Glu Ser Gln Thr Glu Leu Pro Asn Pro
            20              25                      30
Arg Ile Ser Cys Pro Glu Gly Thr Asn Ala Tyr Arg Ser Tyr Cys Tyr
        35              40                      45
Tyr Phe Asn Glu Asp Pro Glu Thr Trp Val Asp Ala Asp Leu Tyr Cys
    50              55                  60
Gln Asn Met Asn Ser Gly Asn Leu Val Ser Val Leu Thr Gln Ala Glu
65              70                  75                      80
Gly Ala Phe Val Ala Ser Leu Ile Lys Glu Ser Ser Thr Asp Asp Ser
            85                  90                  95
Asn Val Trp Ile Gly Leu His Asp Pro Lys Lys Asn Arg Arg Trp His
            100             105                 110
Trp Ser Ser Gly Ser Leu Val Ser Tyr Lys Ser Trp Asp Thr Gly Ser
        115             120                 125
Pro Ser Ser Ala Asn Ala Gly Tyr Cys Ala Ser Leu Thr Ser Cys Ser
    130             135                 140
Gly Phe Lys Lys Trp Lys Asp Glu Ser Cys Glu Lys Lys Phe Ser Phe
145             150                 155                 160
Val Cys Lys Phe Lys Asn
                165
```

HUMAN REG PROTEIN

FIELD OF THE INVENTION

The present invention relates to nucleic acid and amino acid sequences of a novel human Reg protein, which comprises a soluble C-type lectin. This novel human Reg protein shares features with other proteins in the reg/PSP multigene family which are involved in cell growth. The present invention relates to the use of these novel sequences in the diagnosis, prevention and treatment of disease.

BACKGROUND OF THE INVENTION

Lectins are proteins which are defined by their ability to bind carbohydrates specifically and to agglutinate cells. Lectins have been shown to be involved in a wide variety of cellular functions including cell-cell and cell-matrix interactions. Lectins are widespread among plants, invertebrates and mammals.

Animal lectins have been grouped into four distinct families: 1) C-type lectins, which include selecting; 2) P-type lectins; 3) galectins (formerly termed S-type lectins or S-Lac lectins); and 4) pentraxins [Barondes SH et al. (1994) J. Biol. Chem. 269:20807–10]. The C-type lectins bind carbohydrate ligands in a $Ca^{2+}$-dependent manner and are structurally related to the asialoglycoprotein receptor. Selectins, a subcategory of the C-type lectins, are composite transmembrane molecules which are involved in cell-cell interactions. The selectins include lymphocyte homing receptors and platelet/endothelial cell surface receptors [Stoolman (1989) Cell 56:907–10].

C-type animal lectins contain $Ca^{2+}$-dependent carbohydrate-recognition domains (CRDs). The prototypical C-type animal lectins are integral membrane proteins (e.g., the asialoglycoprotein receptor); however, a number of soluble C-type animal lectins have been identified. One group of soluble C-type animal lectins, termed collectins or Group III C-type lectins, comprise proteins having both lectin- (i.e., CRD) and collagenous-like domains within a single polypeptide [Drickamer (1993) Curr. Opin. Struct. Biol. 3:393]. Another group of soluble C-type animal lectins, termed Group IV C-type lectins, comprise free CRDs which are not joined to other polypeptide domains (other than a signal peptide utilized in secretion) [Drickamer (1993), supra]. The soluble C-type animal lectins comprising free CRDs found in mammals are most closely related to proteins identified in invertebrates and lower vertebrates (e.g., snakes).

Proteins recognized as members of the Group IV C-type lectins appear to be members of a multigene family termed the reg/PSP multigene family [Drickamer (1993), supra and Unno et aL (1993) J. Biol. Chem. 268:15974]. The reg/PSP multigene family comprises genes encoding secretory proteins which are expressed in the pancreas; the ectopic expression (i.e., expression in a tissue which does not normally express reg/PSP proteins) of some members of the reg/PSP family is associated with disease states such as tumors and Alzheimer's disease.

The first member of the reg/PSP multigene family was identified in a cDNA library derived from rat regenerating pancreatic islets [Terazono et al. (1988) J. Biol. Chem. 263:2111]. This gene was termed reg (regenerating gene) and is now known as the regI gene; homologs of the rat regIα gene have been identified in humans [Watanabe et al. (1990) J. Biol. Chem. 265:7432] and mice [Unno et al. (1993), supra]. The regIα gene encodes a 166 amino acid protein including a 22 amino acid signal peptide which has been called by different investigators reg protein, regIα protein, lithostathine, islet cell regeneration factor (ICRF), pancreatic stone protein (PSP) and pancreatic thread protein (PTP) [Terazono et al. (1988), supra; Moriizumi et al. (1994) Biochem. Biophys. Acta 1217:199; Dusetti et al. (1993) Biochem. Biophys. Acta 1174:99; Rouquier et al. (1991) J. Biol. Chem. 266:786; and de la Monte et al. (1990) J. Clin. Invest. 86:1004]. The mature form of the regIα/lithostathine protein lacks not only the signal peptide but an additional 11 amino-terminal amino acids which are removed by cleavage by trypsin in pancreatic juice [Giorgi et al. (1989) J. Clin. Invest. 84:100 and Rouimi et al. (1987) FEBS Lett. 216:195].

RegIα mRNA is expressed in normal human tissues most abundantly in the pancreas with moderate expression seen in the gastric mucosa and very low levels of expression in the kidney [Watanabe et al. (1990) J. Biol. Chem. 265:7432]. In the pancreas, regIα protein is expressed at high levels in normal exocrine pancreas cells. No or very low levels of expression are seen in normal islet cells; in contrast, expression of regIα/lithostathine protein is increased dramatically in regenerating islet cells as compared to normal islet cells [Francis et al. (1992) Diabetologia 35:238]. The clear association between reg gene expression and islet cell replication in vitro has lead to the suggestion that the regIα/lithostathine protein has a growth-promoting activity for islet β-cells [Unno et al. (1993), supra].

The regIα/lithostathine protein has been shown to control $CaCO_3$ crystal growth in pancreatic juice [Bernard et al. (1992) Gastroenterol. 103:1277]. RegIα-/lithostathine protein accounts for up to 10% of total protein in pancreatic juice and is present in the pancreatic juice of a variety of mammals including humans, cows, pigs, dogs, rats, and monkeys [Bernard et al. (1991) Pancreas 6:162]. Pancreatic juice is normally supersaturated with bicarbonate and calcium which leads to the formation of $CaCO_3$ crystals. RegIα/lithostathine controls the size of the crystals thereby preventing clogging of pancreatic ducts; a amino-terminal undecapeptide is released from the human reg/lithostathine protein by treatment with trypsin has been shown to contain the inhibitory activity of this protein on $CaCO_3$ crystal growth [Bernard et al. (1992) Gastroenterol. 103:1277]. Patients with chronic calcifying pancreatitis exhibit a reduction in regIα gene expression [Giorgi et al. (1989) J. Clin. Invest. 84:100].

Human regIα mRNA is expressed in colon and rectal tumors although it is not expressed in normal colon or rectal tissue. Thus, ectopic expression of regIα protein is associated with tumorigenesis. Elevated levels of regIα protein has been found in the brains of patients suffering from Alzheimer's disease as well as in the brains of middle-aged individuals with Down's syndrome [Ozturk et al. (1989) Proc. Natl. Acad. Sci. USA 86:419 and de la Monte et al. (1990) J. Clin. Invest. 86:1004]. RegIα mRNA is expressed in the developing human brain, but not in normal adult brain; expression of regIα is seen in adult brain which undergoing regenerative sprouting. Given its pattern of expression (e.g., expression in regenerating pancreatic islets and brain, expression in tumors), it appears that regIα protein is associated with cell growth.

A gene closely related to the regIα gene, called regIβ, has been identified in humans [Moriizumi et al. (1994) Biochem. Biophys. Acta 1217:199]. RegIβ mRNA is appears to be expressed exclusively in the pancreas in contrast to regIα mRNA is expressed in stomach and kidney, as well as in pancreas. The regIβ protein contains 166 amino acids and has a 22 amino acid signal sequence. The regIα and regIβ proteins are 87% identical in amino acid sequence; the regIα and regIβ genes share 91% homology over their respective coding regions.

Other members of the reg/PSP multigene family are the genes encoding pancreatitis-associated proteins (PAPs) which have been identified in humans, mice and rats [Iovanna et al. (1991) J. Biol. Chem. 266:24664; Orelle et aL. (1992) J. Clin. Invest. 90:2284; Itoh and Teraoka (1993) Biochem. Biophys. Acta 1172:184; and Dusetti et al. (1994) Genomics 19:108]. The reg/lithostathine and PAP proteins characterized to date share about 45–65% identity on the amino acid level.

The PAP proteins are secretory proteins which are stored in zymogen granules prior to secretion [Keim et al. (1991) Gastroenterol. 100:775]; PAP is present at low levels in normal pancreas but is rapidly overexpressed during the acute phase of pancreatitis. PAP, like other members of the reg/PSP family, shares sequence similarity with the carbohydrate-binding domain of C-type lectins which likely explains the ability of PAP to induce aggregation of bacteria [Iovanna et al. (1991), supra]. The ability to aggregate bacteria has lead to the suggestion that PAP is involved in the control of bacterial proliferation, a frequent complication of pancreatitis. PAP has been shown to be able to bind lactose [Christa et al. (1994) FEBS Lett. 337:114].

Three PAP genes, PAP I–III, have been identified in rats. All three PAP genes are expressed during the acute phase of pancreatitis. Rat PAP I and PAP III are expressed constitutively in the intestine and their expression is induced by feeding. Rat PAP II is not expressed in the intestine. Rat PAP I and PAP III share 66% amino acid identity; rat PAP II and PAP III share 63% amino acid identity; rat PAP I and PAP II share 58% amino acid identity. A homologue of rat PAP I has been identified in cows [BPTP; de la Monte et al. (1990), supra].

A human homolog of the rat PAP I gene, human PAP or human PAP I, has been identified [Orelle et al. (1992) J. Clin. Invest. 90:2284]. The human PAP I protein is the same size as the rat PAP I protein (175 amino acids) and these two proteins share 71% amino acid identity, including conservation of 7 cystine residues. Expression of the human PAP I mRNA is increased in necrohemorragic pancreatitis. Serum levels of human PAP I were found to be near background levels in normal individuals; in individuals suffering from acute pancreatitis or acute exacerbations of chronic pancreatitis, human PAP I levels increased 24–140 times the background level [Orelle et al. (1992), supra]. Thus, human PAP I appears to serve as a marker of acute pancreatitis.

The human PAP I gene is also referred to as the HIP gene [Lasserre et al. (1992) Cancer Res. 52:5089]. The HIP gene was identified by differential screening of a human primary liver cancer library. The human PAP I/HIP gene is not expressed in normal adult or fetal liver; expression of PAP I/HIP is limited to pancreas and small intestine in normal tissues. Thus, the ectopic expression of PAP I/HIP is associated with tumorigenesis in the liver.

Proteins expressed by the reg/PSP multigene family represent an important family of proteins which are involved in maintenance of proper pancreatic function as well as in regulating cell growth. Discovery of new molecules related to or in the mammalian reg/PSP multigene family is useful for the development of new diagnostic or therapeutic compositions.

SUMMARY

The present invention discloses a novel human reg protein hereinafter referred to as Reg protein Iγ (Reg Iγ), which shares features with human reg proteins Iα and Iβ (Reg Iα and Reg Iβ) and rat lithostathine as well as other members of the reg/PSP multigene family which are involved in maintenance of proper pancreatic function as well as the regulation of cell growth and development, including metastatic potential. Accordingly, the invention provides a substantially purified polypeptide comprising at least a portion of the amino acid sequence of SEQ ID NO:1. In an alternative embodiment, the present invention provides fragments of isolated (i.e., substantially purified) human Reg Iγ of at least 10 amino acid residues in length. The invention further contemplates fragments of isolated human Reg Iγ of at least 25 amino acids, of at least 50 amino acids, at least 100 amino acids, and at least 150 amino acids in length. The invention specifically contemplates secretory (i.e., the signal peptide is cleaved) and nonsecretory (i.e., signal peptide remains) forms of a substantially purified human Reg Iγ as well as any proteolytic fragments thereof.

The present invention further provides an isolated polynucleotide sequence encoding a polypeptide comprising at least a portion of the amino acid sequence of SEQ ID NO: 1. In a preferred embodiment, the isolated polynucleotide comprises at least a portion of the nucleic acid sequence of SEQ ID NO:2 or variants thereof. In another preferred embodiment, the present invention provides polynucleotides comprising fragments of SEQ ID NO:2 having a length greater than 30 nucleotides. The invention further contemplates fragments of this polynucleotide sequence (i.e., SEQ ID NO:2) that are at least 50 nucleotides, at least 100 nucleotides, at least 250 nucleotides, and at least 500 nucleotides in length. The invention specifically contemplates polynucleotides encoding the secretory (i.e., the signal peptide is cleaved) and nonsecretory (i.e., signal peptide remains) forms of human Reg Iγ as well as any proteolytic fragments thereof.

In yet another embodiment, the present invention provides polynucleotide sequences comprising the complement of the nucleic acid sequence of SEQ ID NO:2 or variants thereof; these complementary nucleic acid sequences may comprise the complement of the entire nucleic acid sequence of SEQ ID NO:2 or fragments thereof.

In another embodiment, the present invention provides a polynucleotide sequence that hybridizes under stringent conditions to the nucleic acid sequence of SEQ ID NO:2.

The invention further relates to the nucleic acid sequence encoding human Reg Iγ, oligonucleotides, peptide nucleic acids (PNA), fragments, portions or antisense molecules thereof.

The present invention also provides a method for detecting the presence of polynucleotide sequences encoding at least a portion of human Reg Iγ in a biological sample, comprising the steps of: a) providing: I) a biological sample suspected of containing nucleic acid corresponding to the polynucleotide sequence of SEQ ID NO:2; ii) the polynucleotide of SEQ ID NO:2, or a fragment thereof; b) combining the biological sample with the polynucleotide under conditions such that a hybridization complex is formed between the nucleic acid and the polynucleotide; and c) detecting the hybridization complex. The method of the present invention is not limited by the nature of the nucleic acid corresponding to the polynucleotide sequence of SEQ ID NO:2. In a preferred embodiment, the nucleic acid is ribonucleic acid (RNA) and the detection of a hybridization complex between SEQ ID NO:2 and the RNA correlates with expression of the polynucleotide of SEQ ID NO:2 in the biological sample. In another preferred embodiment, the nucleic acid corresponding to the polynucleotide sequence of SEQ ID NO:2 is deoxyribonucleic acid (DNA) and the detection of a hybridization complex between the DNA in a sample and SEQ ID NO:2 is performed under conditions that permit the detection of alterations (e.g., deletions, translocations, insertions, point mutations, etc.) in the polynucleotide of SEQ ID NO:2 in the biological sample.

The present invention further provides an antisense molecule comprising the nucleic acid sequence complementary to at least a portion of the polynucleotide of SEQ ID NO:2. In another embodiment, the present invention provides a pharmaceutical composition comprising an antisense molecule comprising the nucleic acid sequence complementary to at least a portion of the polynucleotide of SEQ ID NO:2 and a pharmaceutically acceptable excipient.

In another embodiment, the present invention provides an isolated polynucleotide comprising at least a portion of the nucleic acid sequence of SEQ ID NO:2 or variants thereof contained on a recombinant expression vector. In yet another embodiment, the expression vector containing the polynucleotide sequence is contained within a host cell. The invention is not limited by the nature of the host cell employed. For example, the host cell may be an *E. coli* cell, a yeast cell, an insect cell, a mammalian cell, etc.

The present invention further provides a method for producing a polypeptide comprising the amino acid sequence of SEQ ID NO: 1, the method comprising the steps of: a) culturing the host cell containing an expression vector containing an isolated polynucleotide comprising at least a portion of the nucleic acid sequence of SEQ ID NO:2 or variants thereof under conditions suitable for the expression of the polypeptide; and b) recovering the polypeptide from the host cell culture.

In another embodiment, the present invention provides a pharmaceutical composition comprising a substantially purified polypeptide comprising at least a portion of the amino acid sequence of SEQ ID NO:1 and a pharmaceutically acceptable excipient.

The present invention also provides a purified antibody which binds specifically to a polypeptide comprising at least a portion of the amino acid sequence of SEQ ID NO:1. The present invention further provides a pharmaceutical composition comprising a purified antibody which binds specifically to a polypeptide comprising at least a portion of the amino acid sequence of SEQ ID NO:1 and a pharmaceutically acceptable excipient.

The present invention also provides a method for detecting the expression of human Reg Iγ in a biological sample comprising the steps of: a) providing: I) a biological sample suspected of expressing human Reg Iγ protein; and ii) a purified antibody which binds specifically to a polypeptide comprising at least a portion of the amino acid sequence of SEQ ID NO:1; b) combining the biological sample and the antibody under conditions such that an antibody:protein complex is formed; and c) detecting the complex wherein the presence of the complex correlates with the expression of the protein in the biological sample.

BRIEF DESCRIPTION OF THE FIGURES

FIG. 1 shows the amino acid sequence (SEQ ID NO:1) and nucleic acid sequence (SEQ ID NO:2) of human Reg Iγ. The alignment was produced using MacDNAsis™ software (Hitachi Software Engineering Co Ltd, San Bruno, Calif.).

Figure 2:
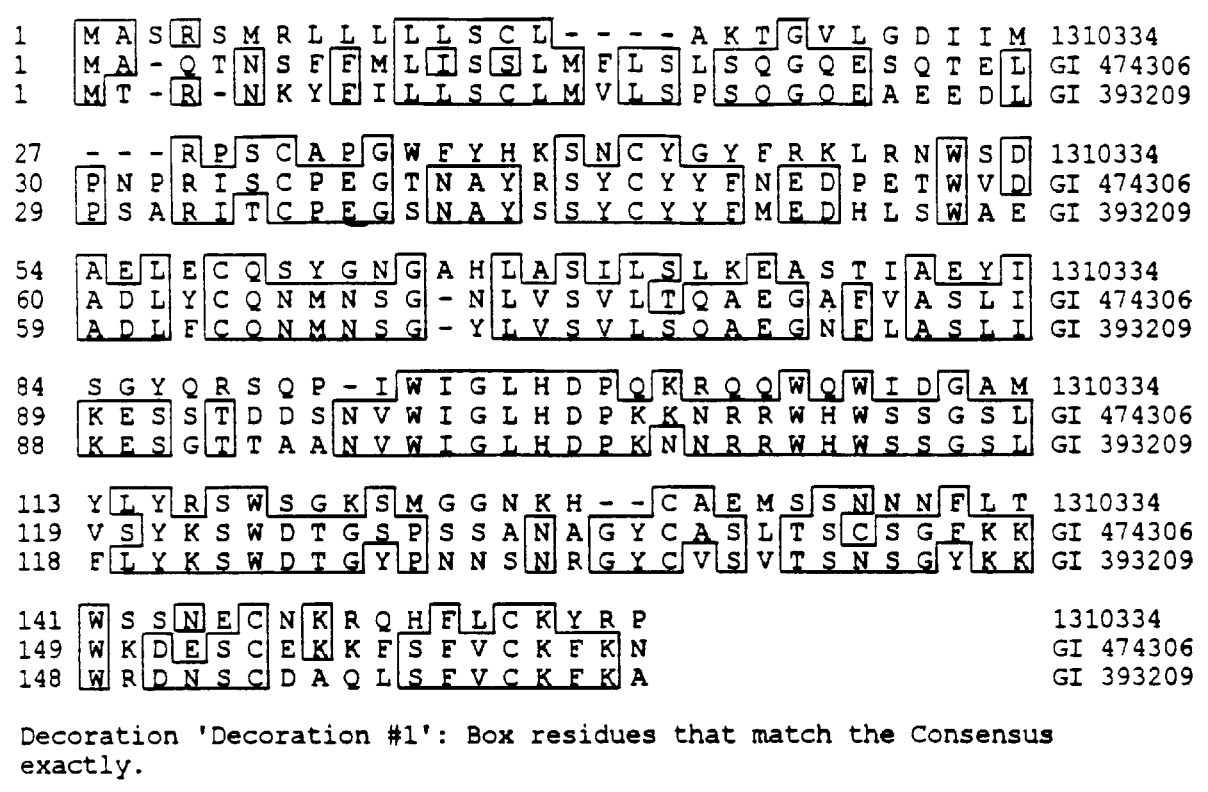

FIG. 2 shows the amino acid sequence alignment between human Reg Iγ (SEQ ID NO:1), human Reg Iβ [GI 474306 (SEQ ID NO:3); Moriizumi et al. (1994), supra] and rat Reg/lithostathine [GI 393209 (SEQ ID NO:4); Dusetti et al. (1993), supra]. These alignments were produced using the multisequence alignment program of DNAStar™ software (DNAStar Inc, Madison Wis.).

FIG. 3 shows the northern analysis for Incyte Clone 1310334 (SEQ ID NO:2). The northern analysis was produced electronically using the LIFESEQ™ database (Incyte Pharmaceuticals, Palo Alto, Calif.) and shows cDNA libraries in which sequences encoding human Reg Iγ were expressed.

FIG. 6 shows the secondary structure for the human Reg Iγ, SEQ ID NO:1, generated using MacDNAsis software.

DESCRIPTION OF THE INVENTION

Definitions

Figure 4:
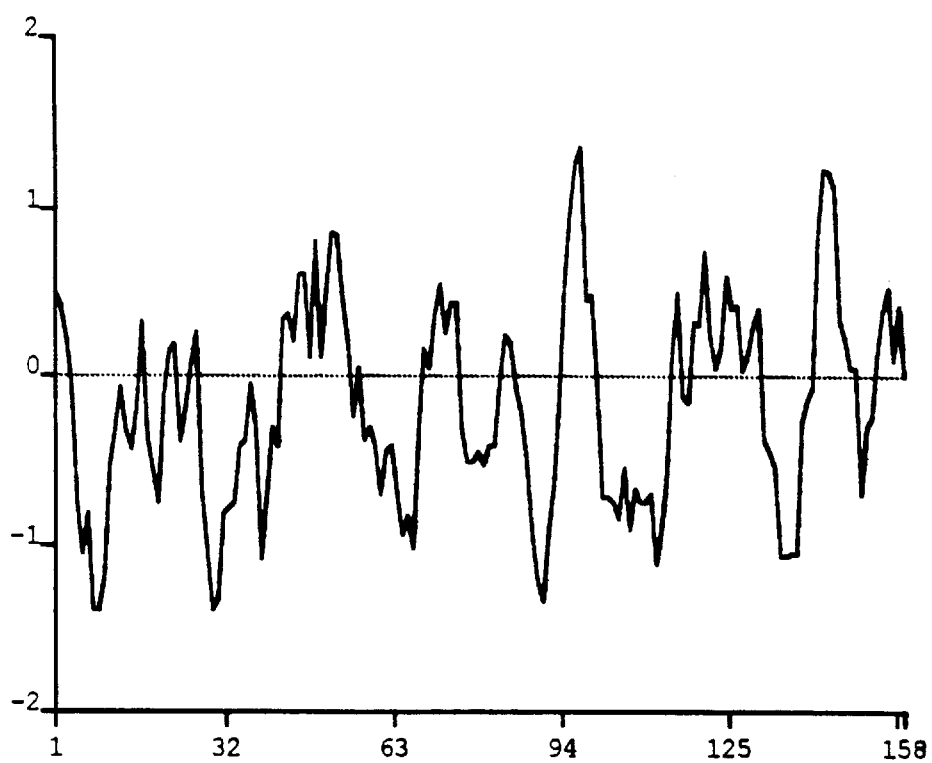
FIG. 4 shows the hydrophobicity plot for human Reg Iγ, SEQ ID NO: 1, generated using MacDNAsis software; the X axis reflects amino acid position, and the negative Y axis, hydrophobicity.
Figure 5:
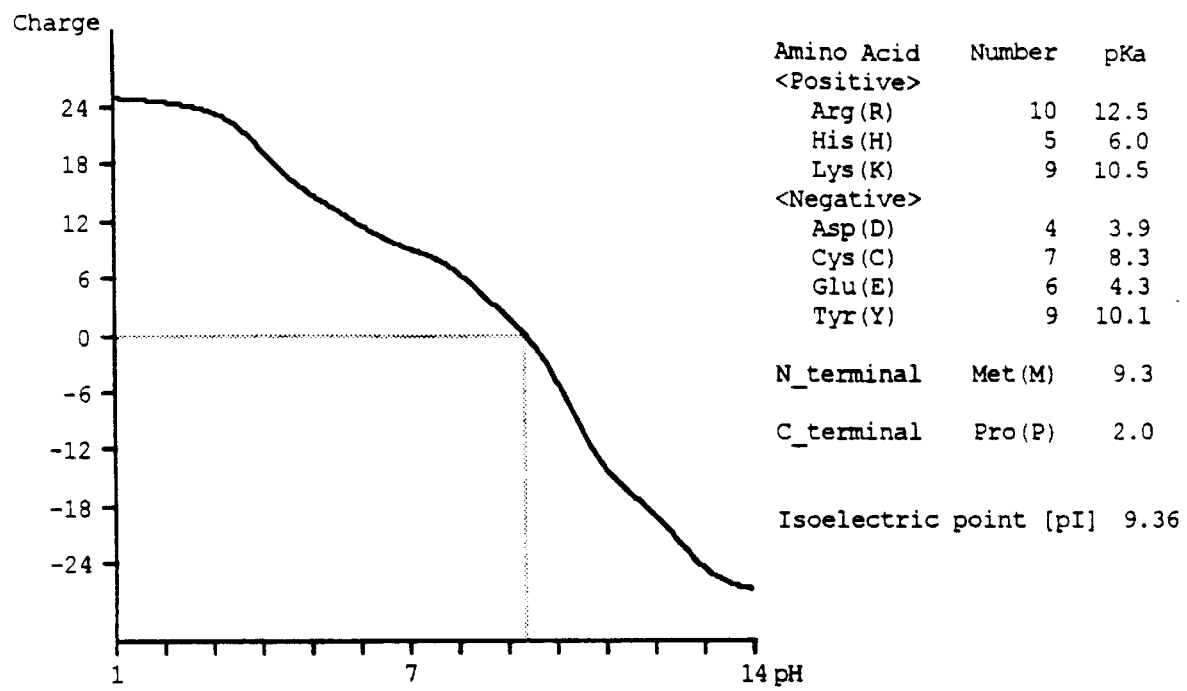
FIG. 5 shows the isoelectric plot for human Reg Iγ, SEQ ID NO:1, generated using MacDNAsis software.

To facilitate understanding of the invention, a number of terms are defined below.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, "amino acid sequence" as used herein refers to peptide or protein sequence.

"Consensus" as used herein may refer to a nucleic acid sequence 1) which has been resequenced to resolve uncalled bases, 2) which has been extended using XL-PCR (Perkin Elmer, Norwalk Conn.) in the 5' or the 3' direction and resequenced, 3) which has been assembled from the overlapping sequences of more than one Incyte clone GCG Fragment Assembly System, (GCG, Madison Wis.), or 4) which has been both extended and assembled.

"Peptide nucleic acid" ("PNA") as used herein refers to a molecule which comprises an oligomer to which an amino acid residue, such as lysine, and an amino group have been added. These small molecules, also designated anti-gene agents, stop transcript elongation by binding to their complementary strand of nucleic acid [Nielsen PE et al. (1993) Anticancer Drug Des 8:53–63].

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, for example, the naturally occurring human Reg Iγ.

A "substitution" results from the replacement of one or more nucleotides or amino acids by different nucleotides or amino acids, respectively.

As used herein the "reg/PSP multigene family" refers to genes encoding any of the following proteins: regenerating protein, reg protein, regIα protein, regIβ, lithostathine, islet cell regeneration factor (ICRF), pancreatic stone protein (PSP), pancreatic thread protein (PTP), HIP protein, pancreatitis-associated protein (PAP) and the novel Reg Iγ of the present invention, as well as other genes which encode proteins sharing at least 21% identity with the listed proteins. Members of the reg/PSP multigene family share a number of features including expression in the pancreas and the presence of sequences conserved among the CRD of C-type lectins. On the amino acid level, members of the reg/PSP multigene family share about 30–87% identity. Protein sequences comprising typical amino acid compositions (i.e., amino acids are present at their observed normal frequencies) which share an identity of greater than 20% are defined as "homologous" or related proteins; this assumes that only a limited number of insertions and deletions are made to align the sequences being compared [Creighton, *Proteins, Structure and Molecular Properties,* 2nd ed., W. H. Freeman, N.Y., pp. 108–109 (1993)].

As used herein, "Reg Iγ" or "Reg protein Iγ" refers to the amino acid sequence of substantially purified Reg Iγ obtained from any species, particularly mammalian, including bovine, ovine, porcine, murine, equine, and preferably human, from any source whether natural, synthetic, semi-synthetic or recombinant.

A "variant" of Reg Iγ is defined as an amino acid sequence differs by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software. Furthermore, as described herein, certain amino acid residues which are highly conserved among mammalian Reg and PAP proteins are located within the CRD of these C-type lectins. It is preferred that these conserved residues not be substituted, inserted or deleted when producing variants of human Reg Iγ.

The term "biologically active" refers to a Reg Iγ molecule having structural, regulatory or biochemical functions of a naturally occurring Reg Iγ. Likewise, "immunologically active" defines the capability of the natural, recombinant or synthetic Reg Iγ, or any oligopeptide thereof, to induce a specific immune response in appropriate animals or cells and to bind with specific antibodies.

The term "derivative" as used herein refers to the chemical modification of a nucleic acid encoding Reg Iγ or the encoded Reg Iγ. Illustrative of such modifications would be replacement of hydrogen by an alkyl, acyl, or amino group. A nucleic acid derivative would encode a polypeptide which retains essential biological characteristics of natural human Reg Iγ.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

"Amplification" is defined as the production of additional copies of a nucleic acid sequence and is generally carried out using polymerase chain reaction technologies well known in the art [Dieffenbach CW and GS Dveksler (1995) *PCR Primer, a Laboratory Manual,* Cold Spring Harbor Press, Plainview N.Y.].

The term "hybridization" as used herein refers to any process by which a strand of nucleic acid joins with a complementary strand through base pairing.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support [e.g., a nylon membrane or a nitrocellulose filter as employed in Southern and Northern blotting, dot blotting or a glass slide as employed in in situ hybridization, including FISH (fluorescent in situ hybridization)].

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5X SSPE (43.8 g/l NaCl, 6.9 g/l $NaH_2PO_4.H_2O$ and 1.85 g/l EDTA, pH adjusted to 7.4 with NaOH), 0.1% SDS, 5X Denhardt's reagent [50X Denhardt's contains per 500 ml: 5 g Ficoll (Type 400, Pharmacia), 5 g BSA (Fraction V; Sigma)] and 100 μg/ml denatured salmon sperm DNA followed by washing in a solution comprising 5X SSPE, 0.1% SDS at 42° C. when a probe of about 500 nucleotides in length is employed.

High stringency conditions comprise conditions equivalent to binding or hybridization at 42° C. in a solution consisting of 5X SSPE (43.8 g/l NaCl, 6.9 g/l $NaH_2PO_4.H_2O$ and 1.85 g/l EDTA, pH adjusted to 7.4 with NaOH), 0.5% SDS, 5X Denhardt's reagent and 100 μg/ml denatured salmon sperm DNA followed by washing in a solution comprising 0.1X SSPE, 1.0% SDS at 42° C. when a probe of about 500 nucleotides in length is employed.

The art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions. The term "hybridization" as used herein includes "any process by which a strand of nucleic acid joins with a complementary strand through base pairing" [Coombs J (1994) *Dictionary of Biotechnology*, Stockton Press, New York N.Y.].

"Stringency" typically occurs in a range from about $T_m$–5° C. (5° C. below the $T_m$ of the probe) to about 20 ° C. to 25 ° C. below $T_m$. As will be understood by those of skill in the art, a stringent hybridization can be used to identify or detect identical polynucleotide sequences or to identify or detect similar or related polynucleotide sequences. Under "stringent conditions" SEQ ID NO:2 or fragments thereof will hybridize to its exact complement and closely related sequences. The stringent conditions are chosen such that SEQ ID NO:2 or fragments thereof will hybridize to sequences encoding human Reg Iγ but not to sequences encoding human Reg Iβ (i.e., SEQ ID NO:3 or its RNA equivalents) or rat Reg/lithostathine (i.e., SEQ ID NO:4 or its RNA equivalents). When fragments of SEQ ID NO:2 are employed in hybridization reactions, the stringent conditions include the choice of fragments of SEQ ID NO:2 to be used. Fragments of SEQ ID NO:2 which contain unique sequences (i.e., regions which are either non-homologous to or which contain less than about 50% homology or complementarity with SEQ ID NOS:5 or 6) are preferentially employed. SEQ ID NOS:5 and 6 represent DNA sequences encoding the human regIβ and rat reg/lithostathine proteins, respectively.

As used herein, the term "antisense" is used in reference to RNA sequences which are complementary to a specific RNA sequence (e.g, mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (–) (i.e., "negative") is sometimes used in reference to the antisense strand, with the designation (+) sometimes used in reference to the sense (i.e., "positive") strand.

As used herein the term "portion" when in reference to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:2" encompasses the full-length human Reg Iγ protein and fragments thereof.

The term "antigenic determinant" as used herein refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample" as used herein is used in its broadest sense. A biological sample suspected of containing nucleic acid encoding human Reg Iγ may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

The term "correlates with expression of a polynucleotide" as used herein indicates that the detection of the presence of ribonucleic acid complementary to SEQ ID NO:2 by hybridization assays is indicative of the presence of mRNA encoding human Reg Iγ in a sample and thereby correlates with expression of the Reg Iγ mRNA from the gene encoding Reg Iγ.

"Alterations in the polynucleotide of SEQ ID NO:2" as used herein comprise any alteration in the sequence of polynucleotides encoding human Reg Iγ including deletions, insertions, and point mutations that may be detected using hybridization assays. Included within this definition is the detection of alterations to the genomic DNA sequence which encodes human Reg Iγ [e.g., by alterations in pattern of restriction enzyme fragments capable of hybridizing to SEQ ID NO:2 (RFLP analysis), the inability of a selected fragment of SEQ ID NO:2 to hybridize to a sample of genomic DNA (e.g., using allele-specific oligonucleotide probes), improper or unexpected hybridization, such as hybridization to a locus other than the normal chromosomal locus for the reg Iγ gene (e.g., using FISH to metaphase chromosomes spreads, etc.)].

Preferred Embodiments

Given the role C-type lectins play in regulating cell growth and development, the discovery of new molecules related to or in the C-type lectin gene family, and in the human reg/PSP multigene family in particular, is useful for developing diagnostic or therapeutic compositions directed at detecting or preventing neoplasia and/or metastasis. In addition, overexpression of Reg proteins is seen in Alzheimer's disease and thus novel human reg genes are useful for developing diagnostic or therapeutic compositions directed at detection and treatment of the neurodegenerative changes associated with Alzheimer's disease and other disorders of the central nervous system (e.g., Down's syndrome).

As aberrant (e.g, ectopic) expression of members within the reg/PSP gene family is associated with tumorigenesis, the discovery of new molecules related to or in the reg/PSP gene family is useful for developing diagnostic or therapeutic compositions directed at a variety of tumors. Furthermore, new molecules related to or in the reg/PSP gene family are useful for developing diagnostic or therapeutic compositions directed at correcting diseases associated with the overexpression or underexpresssion of reg/PSP proteins.

The present invention relates to a novel human Reg Iγ which was initially identified among the partial cDNAs from a fetal colon library (COLNFET02) and to the use of the disclosed nucleic acid and amino acid sequences in the study, diagnosis, prevention and treatment of disease.

The nucleic acid sequence encoding a portion of the novel human Reg Iγ protein was identified in Incyte Clone 1310334 through a computer-generated search for amino acid sequence alignments. The nucleic acid sequence, SEQ ID NO:2, disclosed herein, encodes the amino acid sequence, SEQ ID NO: 1, human Reg Iγ (FIG. 2). The full length cDNA was assembled from Incyte Clones 774137; 775162; 793926; 794035; 794837; 794931; 798309; 815300; 816795; 817375; 1310334; and 1436720 from the LIFESEQ™ database (Incyte Pharmaceuticals, Palo Alto, Calif.).

The human Reg Iγ of the present invention is here described as having 158 amino acid residues, a number of which are residues shown to be conserved among mammalian Reg and PAP proteins and which are conserved among the CRD of C-type animal lectins. The conserved sequence motif found in C-type CRDs is described by Drickamer [Curr. Opin. Struc. Biol. (1993) 3:393] and a version of this motif is found in the PROSITE database as the C-type lectin domain signature (CTL). Sequences corresponding to the CTL within the human Reg Iγ of the present invention include $G_{33}$, $C_{58}$, $G_{95}$, $D_{98}$, $W_{118}$, $C_{129}$, $A_{130}$, $W_{141}$, $C_{146}$, $F_{152}$ and $C_{154}$.

The amino-terminal 23 residues of the human Reg Iγ of the present invention are hydrophobic and likely represent a signal sequence, a feature common to mammalian Reg and PAP proteins.

The human Reg Iγ of the present invention contains seven cysteine residues ($C_{14}$, $C_{30}$, $C_{41}$, $C_{58}$, $C_{129}$, $C_{146}$ and $C_{154}$); six of these seven cysteine residues (i.e., $C_{30}$, $C_{41}$, $C_{58}$, $C_{129}$, $C_{146}$ and $C_{154}$) are conserved between the human Reg Iγ and RegIβ and rat Reg/lithostathine proteins (see alignment shown in FIG. 2; residues are numbered according to SEQ ID NO:1). The human Reg Iγ of the present invention has one potential N-linked glycoslyation sites (i.e., Asn-X-Ser/Thr) (i.e., $N_{50}$). The human Reg Iγ of the present invention contains numerous potential O-linked glycosylation sites (i.e., serine and threonine residues). Other human Reg proteins have been shown to be glycosylated [Watanabe et al. (1990), supra]. In addition, the human Reg Iγ of the present invention contains potential phosphorylation sites (i.e., typically the hydroxyl groups of serine, threonine and tyrosine residues although asparagine, histidine and lysine residues may also be phosphorylated). Serine residues preceded by one or two basic residues are often phosphorylated by Ser/Thr kinases [Creighton, *Proteins, Structure and Molecular Properties*, 2nd ed., W. H. Freeman, NY, pp. 96–97 (1993)]; the novel human Reg Iγ protein disclosed herein contains four such potential phosphorylation sites (i.e., $S_{39}$, $S_{89}$, $S_{117}$, and $S_{122}$). Other human Reg proteins (e.g., human reg/lithostathine/PSP) have been shown to be phosphoglycoproteins containing two to three phosphate groups [Multigener et aL (1985) Gastroenterology 89:387].

The Human Reg Iγ Coding Sequences

The nucleic acid and deduced amino acid sequences of human Reg Iγ are shown in FIGS. 1A and 1B. In accordance with the invention, any nucleic acid sequence which encodes human Reg Iγ can be used to generate recombinant molecules which express human Reg Iγ. In a specific embodiment described herein, a partial sequence encoding human Reg Iγ was first isolated as Incyte Clone 1310334 from a fetal colon cDNA library (COLNFET02).

It will be appreciated by those skilled in the art that as a result of the degeneracy of the genetic code, a multitude of human Reg Iγ-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence encoding naturally occurring human Reg Iγ, and all such variations are to be considered as being specifically disclosed.

Although nucleotide sequences which encode human Reg Iγ and its variants are preferably capable of hybridizing to the nucleotide sequence of the naturally occurring sequence under appropriately selected conditions of stringency, it may be advantageous to produce nucleotide sequences encoding human Reg Iγ or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding human Reg Iγ and its derivatives without altering the encoded amino acid sequences include the production of RNA transcripts having more desirable properties, such as a greater or a shorter half-life, than transcripts produced from the naturally occurring sequence.

It is now possible to produce a DNA sequence, or portions thereof, encoding human Reg Iγ and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding human Reg Iγ or any portion thereof.

Also included within the scope of the present invention are polynucleotide sequences that are capable of hybridizing to the nucleotide sequence of FIG. 1B under various conditions of stringency. Hybridization conditions are based on the melting temperature ($T_m$) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and may be used at a defined "stringency".

Altered nucleic acid sequences encoding human Reg Iγ which may be used in accordance with the invention include deletions, insertions or substitutions of different nucleotides resulting in a polynucleotide that encodes the same or a functionally equivalent human Reg Iγ. The protein may also show deletions, insertions or substitutions of amino acid residues which produce a silent change and result in a functionally equivalent human Reg Iγ. Deliberate amino acid substitutions may be made on the basis of similarity in polarity, charge, solubility, hydrophobicity, hydrophilicity, and/or the amphipathic nature of the residues as long as the biological activity of human Reg Iγ is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles encoding human Reg Iγ. As used herein, an "allele" or "allelic sequence" is an alternative form of the nucleic acid sequence encoding human Reg Iγ. Alleles result from a mutation, i. e., a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (US Biochemical Corp, Cleveland Ohio), Taq DNA polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending The Polynucleotide Sequence

The polynucleotide sequence encoding human Reg Iγ may be extended utilizing partial nucleotide sequence and various methods known in the art to detect upstream sequences such as promoters and regulatory elements. Gobinda et al. (1993; PCR Methods Applic 2:318–22) describe "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al. (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M el al. (1991) PCR Methods Applic 1:111–19), a method for PCR amplification of DNA fragments adjacent to a known sequence in human and yeast artificial chromosome DNA, may also be used. Capture PCR also requires multiple restriction enzyme digestions and ligations to place an engineered double-stranded sequence into an unknown portion of the DNA molecule before PCR.

Another method which may be used to retrieve unknown sequence is walking PCR (Parker JD et al. (1991) Nucleic Acids Res 19:3055–60), a method for targeted gene walking. Alternatively, PCR, nested primers, PromoterFinder™ (Clontech, Palo Alto Calif.) and PromoterFinder libraries can be used to walk in genomic DNA. This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length CDNA. Genomic libraries are useful for extension into the 5' nontranslated regulatory region.

Capillary electrophoresis may be used to analyze either the size or confirm the nucleotide sequence in sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (e.g., Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported [Ruiz-Martinez MC et al. (1993) Anal Chem 65:2851–8].

Expression Of The Nucleotide Sequence

In accordance with the present invention, polynucleotide sequences which encode human Reg Iγ, fragments of the polypeptide, fusion proteins or functional equivalents thereof may be used in recombinant DNA molecules that direct the expression of human Reg Iγ in appropriate host cells. Due to the inherent degeneracy of the genetic code, other DNA sequences which encode substantially the same or a functionally equivalent amino acid sequence, may be used to clone and express human Reg Iγ. As will be understood by those of skill in the art, it may be advantageous to produce human Reg Iγ-encoding nucleotide sequences possessing non-naturally occurring codons. Codons preferred by a particular prokaryotic or eukaryotic host [Murray E et al. (1989) Nuc Acids Res 17:477–508] can be selected, for example, to increase the rate of human Reg Iγ expression or to produce recombinant RNA transcripts having desirable properties, such as a longer or a shorter half-life, than transcripts produced from naturally occurring sequence.

The nucleotide sequences of the present invention can be engineered in order to alter a human Reg Iγ-encoding sequence for a variety of reasons, including but not limited to, alterations which modify the cloning, processing and/or expression of the gene product. For example, mutations may be introduced using techniques which are well known in the art, e.g., site-directed mutagenesis to insert new restriction sites, to alter glycosylation patterns, to change codon preference, to produce splice variants, etc.

In another embodiment of the invention, a natural, modified or recombinant human Reg Iγ-encoding sequence may be ligated to a heterologous sequence to encode a fusion protein. For example, for screening of peptide libraries for inhibitors of human Reg Iγ activity, it may be useful to encode a chimeric human Reg Iγ protein that is recognized by a commercially available antibody. A fusion protein may also be engineered to contain a cleavage site located between a human Reg Iγ and the heterologous protein sequence, so that the human Reg Iγ may be cleaved and substantially purified away from the heterologous moiety.

In an alternate embodiment of the invention, the sequence encoding human Reg Iγ may be synthesized, whole or in part, using chemical methods well known in the art [see Caruthers MH et al. (1980) Nuc Acids Res Symp Ser 215–23, Horn T et al. (1980) Nuc Acids Res Symp Ser 225–32, etc.]. Alternatively, the protein itself could be produced using chemical methods to synthesize a human Reg Iγ amino acid sequence, whole or in part. For example, peptide synthesis can be performed using various solid-phase techniques [Roberge JY et al. (1995) Science 269:202–204] and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography [e.g., Creighton (1983) *Proteins, Structures and Molecular Principles*, WH Freeman and Co, New York N.Y.]. The composition of the synthetic peptides may be confirmed by amino acid analysis or sequencing (e.g., the Edman degradation procedure; Creighton, supra). Additionally the amino acid sequence of human Reg Iγ, or any part thereof, may be altered during direct synthesis and/or combined using chemical methods with sequences from other proteins, or any part thereof, to produce a variant polypeptide.

Expression Systems

In order to express a biologically active human Reg Iγ, the nucleotide sequence encoding human Reg Iγ or its functional equivalent, is inserted into an appropriate expression vector, i.e., a vector which contains the necessary elements for the transcription and translation of the inserted coding sequence.

Methods which are well known to those skilled in the art can be used to construct expression vectors containing a human Reg Iγ-encoding sequence and appropriate transcriptional or translational controls. These methods include in vitro recombinant DNA techniques, synthetic techniques and in vivo recombination or genetic recombination. Such techniques are described in Sambrook et al. (1989) *Molecular Cloning, A Laboratory Manual*, Cold Spring Harbor Press, Plainview N.Y. and Ausubel FM et al. (1989) *Current Protocols in Molecular Biology*, John Wiley & Sons, New York N.Y.

A variety of expression vector/host systems may be utilized to contain and express a human Reg Iγ-encoding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

The "control elements" or "regulatory sequences" of these systems vary in their strength and specificities and are those nontranslated regions of the vector, enhancers, promoters, and 3' and 5' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) or pSport1 (Gibco BRL) and ptrp-lac hybrids and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from the mammalian genes or from mammalian viruses are most appropriate. If it is necessary to generate a cell line that contains multiple copies of the sequence encoding human Reg Iγ, vectors based on SV40 or EBV may be used with an appropriate selectable marker.

In bacterial systems, a number of expression vectors may be selected depending upon the use intended for human Reg Iγ. For example, when large quantities of human Reg Iγ are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the sequence encoding human Reg Iγ may be ligated into the vector in frame with sequences for the amino-terminal Met and the subsequent 7 residues of β-galactosidase so that a hybrid protein is produced; pIN vectors [Van Heeke & Schuster (1989) J Biol Chem 264:5503–5509]; and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al. (supra) and Grant et al. (1987) Methods in Enzymology 153:516–544.

In cases where plant expression vectors are used, the expression of a sequence encoding human Reg Iγ may be driven by any of a number of promoters. For example, viral promoters such as the 35S and 19S promoters of CaMV [Brisson et al. (1984) Nature 310:511–514] may be used alone or in combination with the omega leader sequence from TMV [Takamatsu et al. (1987) EMBO J 6:307–311]. Alternatively, plant promoters such as the small subunit of RUBISCO [Coruzzi et al. (1984) EMBO J 3:1671–1680; Broglie et al. (1984) Science 224:838–843]; or heat shock promoters [Winter J and Sinibaldi RM (1991) Results Probl Cell Differ 17:85–105] may be used. These constructs can be introduced into plant cells by direct DNA transformation or pathogen-mediated transfection. For reviews of such techniques, see Hobbs S or Murry LE in *McGraw Hill Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express human Reg Iγ is an insect system. In one such system, *Autographa californica* nuclear polyhedrosis virus (AcNPV) is used as a vector to express foreign genes in *Spodoptera frugiperda* cells or in *Trichoplusia* larvae. The sequence encoding human Reg Iγ may be cloned into a nonessential region of the virus, such as the polyhedrin gene, and placed under control of the polyhedrin promoter. Successful insertion of the sequence encoding human Reg Iγ will render the polyhedrin gene inactive and produce recombinant virus lacking coat protein. The recombinant viruses are then used to infect *S. frugiperda* cells or *Trichoplusia* larvae in which human Reg Iγ is expressed [Smith et al. (1983) J Virol 46:584; Engelhard EK et al. (1994) Proc Natl Acad Sci 91:3224–7].

In mammalian host cells, a number of viral-based expression systems may be utilized. In cases where an adenovirus is used as an expression vector, a sequence encoding human Reg Iγ may be ligated into an adenovirus transcription/translation complex consisting of the late promoter and tripartite leader sequence. Insertion in a nonessential E1 or E3 region of the viral genome will result in a viable virus capable of expressing in infected host cells [Logan and Shenk (1984) Proc Natl Acad Sci 81:3655–59]. In addition, transcription enhancers, such as the Rous sarcoma virus (RSV) enhancer, may be used to increase expression in mammalian host cells.

Specific initiation signals may also be required for efficient translation of a sequence encoding human Reg Iγ. These signals include the ATG initiation codon and adjacent sequences. In cases where the sequence encoding human Reg Iγ, its initiation codon and upstream sequences are inserted into the most appropriate expression vector, no additional translational control signals may be needed. However, in cases where only coding sequence, or a portion thereof, is inserted, exogenous translational control signals including the ATG initiation codon, and termination codons must be provided. Furthermore, the initiation codon must be in the correct reading frame to ensure translation of the entire insert. Exogenous translational elements and initiation codons can be of various origins, both natural and synthetic. The efficiency of expression may be enhanced by the inclusion of enhancers appropriate to the cell system in use [Scharf D et al. (1994) Results Probl Cell Differ 20:125–62; Bittner et al. (1987) Methods in Enzymol 153:516–544].

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO (ATCC CCL 61 and CRL 9618), HeLa (ATCC CCL 2), MDCK (ATCC CCL 34 and CRL 6253), HEK 293 (ATCC CRL 1573), WI-38 (ATCC CCL 75) (ATCC: American Type Culture Collection, Rockville, Md.), etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express human Reg Iγ may be transformed using expression vectors which contain endogenous expression elements, and may also contain viral origins of replication and a selectable marker gene; the selectable marker gene may be located on the same vector as the Reg Iγ-encoding sequences or may be located on a separate vector which contains sequences which permit expression of the selectable marker gene. Following the introduction of the vector(s), cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transfected cells can be proliferated using tissue culture techniques appropriate to the cell type.

Any number of selection systems may be used to recover transfected cell lines. These include, but are not limited to, the herpes simplex virus thymidine kinase (Wigler M et al. (1977) Cell 11:223–32) and adenine phosphoribosyltransferase (Lowy I et al. (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate [Wigler M et al. (1980) Proc Natl Acad Sci 77:3567–70]; npt, which confers resistance to the aminoglycosides neomycin and G-418 [Colbere-Garapin F et al. (1981) J Mol Biol 150:1–14] and als orpat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine [Hartman SC and RC Mulligan (1988) Proc Natl Acad Sci 85:8047–51]. Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system [Rhodes CA et al. (1995) Methods Mol Biol 55:121–131].

Identification Of Transformants Containing The Polynucleotide Sequence

Although the presence/absence of marker gene expression suggests that the gene of interest is also present, its presence and expression should be confirmed. For example, if the sequence encoding human Reg Iγ is inserted within a marker gene sequence, recombinant cells containing the sequence encoding human Reg Iγ can be identified by the absence of marker gene function. Alternatively, a marker gene can be placed in tandem with the sequence encoding human Reg Iγ under the control of a single promoter. Expression of the marker gene in response to induction or selection usually indicates expression of the tandem sequence as well.

Alternatively, host cells which contain the coding sequence for human Reg Iγ and express human Reg Iγ may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding human Reg Iγ can be detected by DNA-DNA or DNA-RNA hybridization or amplification using probes, portions or fragments of the sequence encoding human Reg Iγ. Nucleic acid amplification based assays involve the use of oligonucleotides or oligomers based on the nucleic acid sequence to detect transformants containing DNA or RNA encoding human Reg Iγ. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of human Reg Iγ, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on human Reg Iγ is preferred, but a competitive binding assay may be employed. These and other assays are described, among other places, in Hampton R et al. (1990, *Serological Methods a Laboratory Manual*, APS Press, St Paul Minn.) and Maddox DE et al. (1983, J Exp Med 158:1211).

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the human Reg Iγ-encoding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like.

Purification Of Human Reg Iγ

Host cells transformed with a nucleotide sequence encoding human Reg Iγ may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing human Reg Iγ-encoding sequence can be designed with signal sequences which direct secretion of human Reg Iγ through a prokaryotic or eukaryotic cell membrane; the naturally occurring Reg Iγ signal sequence may be utilized or alternatively, heterologous signal sequences derived from prokaryotic or eukaryotic genes may be employed. Further, the art understands that where secretion of human Reg Iγ is not desired, sequences encoding the naturally-occurring human Reg Iγ signal sequence are not employed on expression vectors containing human Reg Iγ gene sequences.

Human Reg Iγ may also be expressed as a recombinant protein with one or more additional polypeptide domains added to facilitate purification of soluble proteins. Such purification facilitating domains include, but are not limited to, metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequences such as Factor XA or enterokinase (Invitrogen, San Diego Calif.) between the purification domain and human Reg Iγ is useful to facilitate purification. One such expression vector provides for expression of a fusion protein comprising the sequence encoding human Reg Iγ and nucleic acid sequence encoding 6 histidine residues followed by thioredoxin and an enterokinase cleavage site. The histidine residues facilitate purification while the enterokinase cleavage site provides a means for purifying human Reg Iγ from the fusion protein. Literature pertaining to vectors containing fusion proteins is available in the art [see, for example, Kroll DJ et al. (1993) DNA Cell Biol 12:441–53].

In addition to recombinant production, fragments of human Reg Iγ may be produced by direct peptide synthesis using solid-phase techniques [cf Stewart et al. (1969) *Solid-Phase Peptide Synthesis*, WH Freeman Co, San Francisco; Merrifield J (1963) J Am Chem Soc 85:2149–2154]. In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of human Reg Iγ may be chemically synthesized separately and combined using chemical methods to produce the full length molecule.

Uses Of Human Reg Iγ

The rationale for use of the nucleotide and peptide sequences disclosed herein is based in part on the chemical and structural homology among the novel human Reg Iγ protein and the human Reg Iβ [GI 474306; Moriizumi et al. (1994), supra] and rat reg/lithostathine proteins [GI 393209; Dusetti et al. (1993), supra]. In addition, the novel human Reg Iγ protein shares structural features with several other proteins in the reg/PSP multigene family, including amino acid sequences which are conserved among the CRD of C-type lectins. Lectins are involved in a variety of cellular functions including cell-cell and cell-matrix interactions; aberrant expression of some lectins is associated with tumorigenesis and/or metastasis. Indeed, aberrant expression of some members of the reg/PSP multigene family is associated with a variety of disease states. For example, overexpression of human regIα is observed in human colon and rectal tumors [Watanabe et al. (1990), supra]. Overexpression of human regIα is observed in the brains of Alzheimer's patients and in the brains of middle-age Down's syndrome patients [de la Monte et al. (1990), supra]. Brains from these patients show an accumulation of paired helical filaments which are similar to the filamentous bundles formed by regIα protein in vitro (hence some investigators termed this protein pancreatic thread protein) [Gross et al. (1985) Proc. Natl. Acad. Sci. USA 82:5627]. Expression of the human PAP I/HIP gene in adult liver is associated with liver cancer; PAPI/HIP is not expressed in normal adult or fetal liver [Lasserre et al. (1992), supra]. PAP proteins are overexpressed in the pancreas of individuals suffering from acute pancreatitis and thus serve as markers for this disease [Orelle et al. (1992), supra].

Proteins within the reg/PSP multigene family are expressed in the pancreas. As demonstrated herein, the human Reg Iγ of the present invention, like other reg/PSP genes, is expressed in pancreas. In addition, as shown herein, human Reg Iγ is expressed most abundantly in human ovary and in ovarian tumor tissue with lower levels of expression in colon tissue. As other investigations failed to examine the expression of reg/PSP family members in ovarian tissue, it is not known whether the abundant expression of human RegIγ in the ovary is a feature unique to this novel gene or whether this is a characteristic shared by other reg/PSP family members.

Ectopic expression or the perturbations of the normal pattern of expression of reg/PSP proteins has been shown to be associated with a variety of disease states, including tumors and neurodegenerative diseases; therefore, the human Reg Iγ nucleic and amino acid sequences of the present invention are useful in the development of diagnostics for the detection of tumors and other diseases. The nucleotide sequence may be used in hybridization or PCR technologies to diagnose the induced expression of Reg Iγ sequences early in the disease process. Likewise the protein can be used to produce antibodies useful in ELISA assays or a derivative diagnostic format (as discussed in detail below).

In order to provide a basis for diagnosis, normal or standard values for human Reg Iγ mRNA expression must be established. This is accomplished by quantitating the amount of Reg Iγ mRNA in tissues taken from normal subjects, either animal or human, with nucleic probes derived from the Reg Iγ sequences provided herein (either DNA or RNA forms) using techniques which are well known in the art (e.g., Southern blots, Northern blots, dot or slot blots). The standard values obtained from normal samples may be compared with values obtained from samples from subjects potentially affected by disease (e.g., tumors, Alzheimer's, chronic calcifying pancreatitis or other disorders of the pancreas). Deviation between standard and subject values establishes the presence of a disease state.

The nucleotide sequence encoding human Reg Iγ is useful when placed in an expression vector for making quantities of protein for therapeutic use. The antisense nucleotide sequence of the human Regγ gene is potentially useful in vectors designed for gene therapy directed at neoplasia including metastases. Additionally, the inhibition of human Reg Iγ expression may be useful in alleviating the neurodegenerative changes associated with disorders such as Alzheimer's disease. Alternatively, the human Reg Iγ-encoding nucleotide sequence may used to direct the expression of human Reg Iγ in situations where it is desirable to increase the amount of human Reg Iγ (e.g., for disorders associated with low or nonexistent level of expression of Reg Iγ or to induce or aid in the regeneration of pancreatic islet cells). Even the transient expression or delivery of human Reg Iγ to cells and tissues may be therapeutic. The expression of reg/PSP proteins is important for proper pancreatic function and therefore the ability to increase the level of expression of human Reg Iγ in patients which fail to express normal levels of Reg Iγ in the pancreas is therapeutic.

Human Reg Iγ Antibodies

Human Reg Iγ-specific antibodies are useful for the diagnosis and treatment of conditions and diseases associated with expression of human Reg Iγ (including the overexpression and the absence of expression). Such antibodies include, but are not limited to, polyclonal, monoclonal, chimeric, single chain, Fab fragments and fragments produced by a Fab expression library. Neutralizing antibodies, i.e., those which inhibit dimer formation, are especially preferred for diagnostics and therapeutics.

Human Reg Iγ protein to be used for antibody induction need not retain biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of human Reg Iγ amino acids may be fused with those of another protein such as keyhole limpet hemocyanin and antibody produced against the chimeric molecule.

For the production of antibodies, various hosts including goats, rabbits, rats, mice, etc may be immunized by injection with human Reg Iγ or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guerin) and *Corynebacterium parvum* are potentially useful adjuvants.

Monoclonal antibodies to human Reg Iγ may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al. (1983) Immunol Today 4:72; Cote et al. (1983) Proc Natl Acad Sci 80:2026–2030) and the EBV-hybridoma technique [Cole et al. (1985) *Monoclonal Antibodies and Cancer Therapy*, Alan R Liss Inc, New York N.Y., pp 77–96].

In addition, techniques developed for the production of "chimeric antibodies", the splicing of mouse antibody genes to human antibody genes to obtain a molecule with appropriate antigen specificity and biological activity can be used [Morrison et al. (1984) Proc Natl Acad Sci 81:6851–6855; Neuberger et al. (1984) Nature 312:604–608; Takeda et al. (1985) Nature 314:452–454]. Alternatively, techniques described for the production of single chain antibodies (U.S. Pat. No. 4,946,778) can be adapted to produce human Reg Iγ-specific single chain antibodies.

Antibodies may also be produced by inducing in vivo production in the lymphocyte population or by screening recombinant immunoglobulin libraries or panels of highly specific binding reagents as disclosed in Orlandi et al. (1989, Proc Natl Acad Sci 86:3833–3837), and Winter G and Milstein C (1991; Nature 349:293–299).

Antibody fragments which contain specific binding sites for human Reg Iγ may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity [Huse WD et al. (1989) Science 256:1275–1281].

A variety of protocols for competitive binding or immunoradiometric assays using either polyclonal or monoclonal antibodies with established specificities are well known in the art. Such immunoassays typically involve the formation of complexes between human Reg Iγ and its specific antibody and the measurement of complex formation. A two-site, monoclonal-based immunoassay utilizing monoclonal antibodies reactive to two noninterfering epitopes on a specific human Reg Iγ protein is preferred, but a competitive binding assay may also be employed. These assays are described in Maddox DE et aL (1983, JExp Med 15 8:1211).

Diagnostic Assays Using Human Reg Iγ Specific Antibodies

Particular human Reg Iγ antibodies are useful for the diagnosis of conditions or diseases characterized by expression of human Reg Iγ or in assays to monitor patients being treated with human Reg Iγ, its fragments, agonists or inhibitors (including antisense transcripts capable of reducing expression of human Reg Iγ). Diagnostic assays for human Reg Iγ include methods utilizing the antibody and a label to detect human Reg Iγ in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring human Reg Iγ, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on human Reg Iγ is preferred, but a competitive binding assay may be employed. These assays are described, among other places, in Maddox, DE et al. (1983, J Exp Med 158:1211).

In order to provide a basis for diagnosis, normal or standard values for human Reg Iγ expression must be established. This is accomplished by combining body fluids or cell extracts taken from normal subjects, either animal or human, with antibody to human Reg Iγ under conditions suitable for complex formation which are well known in the art. The amount of standard complex formation may be quantified by comparing various artificial membranes containing known quantities of human Reg Iγ with both control and disease samples from biopsied tissues. Then, standard values obtained from normal samples may be compared with values obtained from samples from subjects potentially affected by disease (e.g., metastases, Alzheimer's disease, chronic calcifying pancreatitis or other disorders of the pancreas). Deviation between standard and subject values establishes the presence of a disease state.

Drug Screening

Human Reg Iγ, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between human Reg Iγ and the agent being tested, may be measured.

Another technique for drug screening which may be used for high throughput screening of compounds having suitable binding affinity to the human Reg Iγ is described in detail in "Determination of Amino Acid Sequence Antigenicity" by Geysen HN, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of human Reg Iγ and washed. Bound human Reg Iγ is then detected by methods well known in the art. Substantially purified human Reg Iγ can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding human Reg Iγ specifically compete with a test compound for binding human Reg Iγ. In this manner, the antibodies can be used to detect the presence of any peptide which shares one or more antigenic determinants with human Reg Iγ.

Uses Of The Polynucleotide Encoding Human Reg Iγ

A polynucleotide sequence encoding human Reg Iγ or any part thereof may be used for diagnostic and/or therapeutic purposes. For diagnostic purposes, the sequence encoding human Reg Iγ of this invention may be used to detect and quantitate gene expression in biopsied tissues in which human Reg Iγ may be expressed. The diagnostic assay is useful to distinguish between absence, presence, and excess expression of human Reg Iγ and to monitor regulation of human Reg Iγ levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding human Reg Iγ or closely related molecules. The specificity of the probe, whether it is made from a highly specific region, e.g., 10 unique nucleotides in the 5' regulatory region, or a less specific region, e.g., especially in the 3' region, and the stringency of the hybridization or amplification (maximal, high, intermediate or low) will determine whether the probe identifies only naturally occurring human Reg Iγ, alleles or related sequences.

Probes may also be used for the detection of related sequences and should preferably contain at least 50% of the nucleotides from any of these human Reg Iγ-encoding sequences. The hybridization probes of the subject invention may be derived from the nucleotide sequence of SEQ ID NO:2 or from genomic sequence including promoter, enhancer elements and introns of the naturally occurring sequence encoding human Reg Iγ. Hybridization probes may be labeled by a variety of reporter groups, including radionuclides such as $^{32}P$ or $^{35}S$, or enzymatic labels such as alkaline phosphatase coupled to the probe via avidinibiotin coupling systems, and the like.

Other means for producing specific hybridization probes for DNAs include the cloning of nucleic acid sequences encoding human Reg Iγ or human Reg Iγ derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding human Reg Iγ may be used for the diagnosis of conditions or diseases with which the expression of human Reg Iγ is associated. For example, polynucleotide sequences encoding human Reg Iγ may be used in hybridization or PCR assays of fluids or tissues from biopsies to detect human Reg Iγ expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The human Reg Iγ-encoding nucleotide sequences disclosed herein provide the basis for assays that detect activation or induction associated with disease (including metastasis); in addition, the lack of expression of human Reg Iγ may be detected using the human Reg Iγ-encoding nucleotide sequences disclosed herein. The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding human Reg Iγ in the sample indicates the presence of the associated inflammation and/or disease. Alternatively, the loss of expression of human Reg Iγ sequences in a tissue which normally expresses human Reg ly sequences indicates the presence of an abnormal or disease state.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for human Reg Iγ expression must be established. This is accomplished by combining body fluids or cell extracts taken from normal subjects, either animal or human, with human Reg Iγ, or a portion thereof, under conditions suitable for hybridization or amplification. Standard hybridization may be quantified by comparing the values obtained for normal subjects with a dilution series of human Reg Iγ run in the same experiment where a known amount of substantially purified human Reg Iγ is used. Standard values obtained from normal samples may be compared with values obtained from samples from patients affected by human Reg Iγ-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, may be used and provides additional uses for oligonucleotides based upon the sequence encoding human Reg Iγ. Such oligomers are generally chemically synthesized, but they may be generated enzymatically or produced from a recombinant source. Oligomers generally comprise two nucleotide sequences, one with sense orientation (5'Δ3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling [Melby PC et al. (1993) J Immunol Methods 159:235–44] or biotinylating [Duplaa C et al. (1993) Anal Biochem 229–36] nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to mammalian reg/PSP proteins and its expression profile, the polynucleotide encoding human Reg Iγ disclosed herein may be useful in the treatment of diabetes (e.g., to induce regeneration of pancreatic β-cells). In addition, as the overexpression of other reg/PSP proteins has been shown to correlate with tumorigenesis and neurodegeneration, inhibition of human Reg Iγ expression may be therapeutic.

Expression vectors derived from retroviruses, adenovirus, herpes or vaccinia viruses, or from various bacterial plasmids, may be used for delivery of nucleotide sequences (sense or antisense) to the targeted organ, tissue or cell population. Methods which are well known to those skilled in the art can be used to construct recombinant vectors which will express antisense of the sequence encoding human Reg Iγ. See, for example, the techniques described in Sambrook et al. (supra) and Ausubel et al. (supra).

The polynucleotides comprising full length cDNA sequence and/or its regulatory elements enable researchers to use the sequence encoding human Reg Iγ as an investigative tool in sense [Youssoufian H and HF Lodish 1993 Mol Cell Biol 13:98–104] or antisense [Eguchi et al. (1991) Annu Rev Biochem 60:631–652] regulation of gene function. Such technology is now well known in the art, and sense or antisense oligomers, or larger fragments, can be designed from various locations along the coding or control regions.

Genes encoding human Reg Iγ can be turned off by transfecting a cell or tissue with expression vectors which express high levels of a desired human Reg Iγ fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA or PNA, to the control regions of the sequence encoding human Reg Iγ, i.e., the promoters, enhancers, and introns. Oligonucleotides derived from the transcription initiation site, e.g., between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee JE et al. [In: Huber BE and BI Carr (1994) Molecular and Immunologic Approaches, Futura Publishing Co, Mt Kisco N.Y.].

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding human Reg Iγ.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding human Reg Iγ. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences encoding human Reg Iγ disclosed herein may be used in molecular biology techniques that have not yet been developed, provided the new techniques rely on properties of nucleotide sequences that are currently known, including but not limited to such properties as the triplet genetic code and specific base pair interactions.

Detection And Mapping Of Related Polynucleotide Sequences

The nucleic acid sequence encoding human Reg Iγ can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price CM (1993; Blood Rev 7:127–34) and Trask BJ (1991; Trends Genet 7:149–54).

The technique of fluorescent in situ hybridization (FISH) of chromosome spreads has been described, among other places, in Verma et al. (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981 f). Correlation between the location of a the sequence encoding human Reg Iγ on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research [Hudson TJ et al. (1995) Science 270:1945–1954]. Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 [Gatti et al. (1988) Nature 336:577–580], any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration Of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, e.g., by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of human Reg Iγ, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, e.g., tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that human Reg Iγ can be used as a therapeutic molecule to induce cell growth (e.g., to induce regeneration of pancreatic β-cells). It is further contemplated that antisense molecules capable of reducing the expression of human Reg Iγ can be as therapeutic molecules to treat tumors associated with the aberrant expression of human Reg Iγ. Still further it is contemplated that antibodies directed against human Reg Iγ and capable of neutralizing the biological activity of human Reg Iγ may be used as therapeutic molecules to treat tumors associated with the aberrant expression of human Reg Iγ.

The examples below are provided to illustrate the subject invention and are not included for the purpose of limiting the invention.

EXAMPLES

I. COLNFET02 cDNA Library Construction

The COLNFET02 CDNA library was constructed from colon tissue obtained from a 20-week-old Caucasian female fetus. The pregnant mother was treated with erythromycin for seven days in the first trimester for bronchitis (specimen #RU95-10-0739; IIAM, Exton, Pa.).

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the Qiagen Oligotex kit (QIAGEN, Inc., Chatsworth, Calif.) and used to construct the cDNA library.

The mRNA was handled according to the recommended protocols in the SuperScript Plasmid System for cDNA Synthesis and Plasmid Cloning (Cat. #18248-013, Gibco/BRL). The commercial plasmid pSPORT 1 (Gibco/BRL) was digested with EcoRi restriction enzyme (New England Biolabs, Beverley, Mass.). The overhanging ends of the plasmid were filled in using Klenow enzyme (New England Biolabs) and 2'-deoxynucleotide 5'triphosphates (dNTPs). The plasmid was self-ligated and transformed into the bacterial host, $E.$ $coli$ strain JM 109. An intermediate plasmid produced by the bacteria failed to digest with EcoRI confirming the desired loss of the EcoRI restriction site.

This intermediate plasmid (pSPORT 1-ΔRI) was then digested with HindIII restriction enzyme (New England Biolabs) and the overhang was filled in with Klenow and dNTPs. A 10-mer linker of sequence 5'. . . CGGAATTCCG . . . 3' was phosphorylated and ligated onto the blunt ends. The product of the ligation reaction was digested with EcoRI and self-ligated. Following transformation into JM 109 host cells, plasmids were isolated and screened for the digestibility with EcoRI but not with HindIII. A single colony which met this criteria was designated pINCY 1. The plasmid produced by this colony was sequenced and found to contain several copies of the 10-mer linker. These extra linkers did not present a problem as they were eliminated when the vector was prepared for cloning.

The plasmid was tested for its ability to incorporate cDNAs from a library prepared using NotI and EcoRI restriction enzymes. Several clones were sequenced and a single clone containing an insert of approximately 0.8 kb was selected to prepare a large quantity of the plasmid for library production. After digestion with NotI and EcoRI, the plasmid and the cDNA insert were isolated on an agarose gel and the vector was purified on a QIAQuick (Qiagen, Inc., Chatsworth, Calif.) column for use in library construction.

cDNAs were fractionated on a Sepharose CL4B column (Cat. #275105-01, Pharmacia), and those cDNAs exceeding 400 bp were ligated into pSport I. The plasmid pSport I was subsequently transformed into DH5α™ competent cells (Cat. #18258-012, Gibco/BRL).

II. Isolation and Sequencing of cDNA Clones

Plasmid DNA was released from the cells and purified using the REAL Prep 96 Plasmid Kit for Rapid Extraction Alkaline Lysis Plasmid Minipreps (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

Most of the sequences disclosed herein were sequenced according to standard ABI protocols, using ABI kits (Cat. Nos. 79345, 79339, 79340, 79357, 79355). The solution volumes were used at 0.25x - 1.0x concentrations. Some of the sequences disclosed herein were sequenced using different solutions and dyes which, unless otherwise noted, came from Amersham Life Science (Cleveland, Ohio).

First, stock solutions were prepared with HPLC water. The following solutions were each mixed by vortexing for 2 min: 1) Tris-EDTA (TE) Buffer was prepared by adding 49 ml water to 1 ml 50x Tris-EDTA concentrate, and 2) 10% Reaction Buffer was prepared by adding 45 ml water to 5 ml Concentrated Thermo Sequenase (TS) Reaction Buffer.

Second, 0.2 μM energy transfer (ET) primers were prepared in the following manner. Each primer tube was centrifuged prior to opening to assure that all primer powder was on the bottom of the tube. After each solubilization step, the mixture was vortexed for 2 min and then centrifuged for about 10 sec in a table-top centrifuge. 1 ml of 1x TE was added to each primer powder; adenine and cytosine dissolved primers (5-carboxyrhodamine-6G (R6G) and 6-carboxyfluorescein (FAM), respectively), were diluted with 9 ml 1x TE. Guanine and thymine dyes (N,N,N',N"-tetramethyl 6-carboxyrhodamine (TAM) and 6-carboxy-X-rhodamine (ROX), respectively) were diluted with 19 ml 1x TE.

Next, the sequencing reaction ready mix was prepared as follows: 1) nucleotides A and C (8 ml of each) were added to 6 ml ET primer and 18 ml TS reaction buffer; and 2) nucleotides G and T (8 ml of each) were added to 6 ml ET primer and 18 ml TS reaction buffer.

After vortexing for 2 min and centrifuging for 20 sec, the resulting solution was divided into tubes in volumes of 8 ml per tube in order to make 1x (A,C) and 2x (G,T) solutions.

Prior to thermal cycling, each nucleotide was individually mixed with DNA template in the following proportions:

| Reagent | A(μL) | C(μL) | G(μL) | T(μL) |
|---|---|---|---|---|
| Reaction Ready Premix | 2 | 2 | 4 | 4 |
| DNA Template | 1 | 1 | 2 | 2 |
| Total Volume | 3 | 3 | 6 | 6 |

These solutions underwent the following thermal cycling:
1. Rapid thermal ramp to 94° C. (94° C. for 20 sec)*
2. Rapid thermal ramp to 50° C. (50° C. for 40 sec)*
3. Rapid thermal ramp to 68° C. (68° C. for 60 sec)*
   * Steps 1, 2, and 3 were repeated for 15 cycles
4. Rapid thermal ramp to 94° C. (94° C. for 20 sec)**
5. Rapid thermal ramp to 68° C. (68° C. for 60 sec)**
   ** Steps 4 and 5 were repeated for 15 cycles
6. Rapid thermal ramp to 4° C. and hold until ready to combine.

After thermal cycling, the A, C, G, and T reactions with each DNA template were combined. Then, 50 μL 100% ethanol was added and the solution was spun at 4° C. for 30 min. The supernatant was decanted and the pellet was rinsed with 100 μL 70% ethanol. After being spun for 15 min, the supernatant was discarded and the pellet was dried for 15 min under vacuum. The DNA sample was dissolved in 3 μL of formaldehyde/50 mM EDTA. The resulting samples were loaded on wells in volumes of 2 μL per well for sequencing in ABI sequencers.

III. Homology Searching of cDNA Clones and Their Deduced Proteins

Each cDNA was compared to sequences in GenBank using a search algorithm developed by Applied Biosystems and incorporated into the INHERIT- 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J Mol Evol 36:290–300; Altschul, SF et al. (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

A comparison of the full-length and partial cDNA sequences and the deduced amino acid sequences corresponding to the human reg Iγ gene and Reg Iγ protein with known nucleotide and protein sequences in GenBank revealed that the full-length human Reg Iγ cDNA and protein sequences (i.e., SEQ ID NOs:1 and 2) were unique (i.e., not previously identified). Thus, SEQ ID NO:1 represents the first identified human Reg Iγ homolog. This search revealed that the human Reg Iγ protein shared some homology with the human Reg Iβ and rat reg/lithostathine proteins (see alignment in FIG. 2); more limited homology with nucleotide sequences encoding the human Reg Iβ and rat reg/lithostathine proteins was found.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul SF 1993 and 1990, supra) are used to search for identical or related molecules in nucleotide databases such as GenBank or the LIFESEQ™ database (Incyte, Palo Alto Calif.) (this technique is termed an "electronic northern"). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding human galectin-8 occurs. Abundance and percentage abundance are also reported. Abundance directly reflects the number of times a particular transcript is represented in a cDNA library, and percent abundance is abundance divided by the total number of sequences examined in the cDNA library.

Electronic northern analysis (FIG. 3) revealed that mRNA encoding human Reg Iγ (SEQ ID NO:1) was present in libraries generated from the following tissues: ovary (Incyte library: OVARNOT03); ovarian tumor (Incyte library: OVARTUT01); colon (Incyte library: COLNNOT05); pancreas (Incyte library: PANCNOT08); and fetal colon (Incyte library: COLNFET02). This analysis revealed that human Reg Iγ transcripts were most abundant in adult ovary the tissues examined. In addition, this analysis revealed that human Reg Iγ transcripts were expressed in tumor tissue (ovarian tumor). The Northern analysis showed that human Reg Iγ transcripts were expressed in the pancreas, a feature in common with other members of the reg/PSP multigene family.

V. Extension Of The Sequence Encoding Human Reg Iγ

The nucleic acid sequence of SEQ ID NO:2 is used to design oligo-nucleotide primers for extending a partial nucleotide sequence to full length or for obtaining 5' sequence from genomic libraries. One primer is synthesized to initiate extension in the antisense direction (XLR) and the other is synthesized to extend sequence in the sense direction (XLF). Primers allow the extension of the know sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and cut out of the gel. Further purification involves using a commercial gel extraction method such as QIAQuick™ (QIAGEN Inc). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook J et al., supra). After incubation for one hour at 37° C., the whole transformation mixture is plated on Luria Bertani (LB)-agar (Sambrook J et al., supra) containing 2xCarb. The following day, several colonies are randomly picked from each plate and cultured in 150 µl of liquid LB/2xCarb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3x) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial eDNAs, and appropriate clones are selected, ligated into plasmid and sequenced.

VI. Labeling And Use Of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [γ-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (AseI, BglII, EcoRI, PstI, XbaI, or PvuII; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1 x saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII. Antisense Molecules

The sequence encoding human Reg Iγ, or any part thereof, is used to inhibit in vivo or in vitro expression of the naturally occurring sequence. Although use of antisense oligonucleotides, comprising about 20 base-pairs, is specifically described, essentially the same procedure is used with larger cDNA fragments. An oligonucleotide complementary to the coding sequence of human Reg Iγ as shown in FIGS. 1A and 1B is used to inhibit expression of the naturally occurring sequence. The complementary oligonucleotide is designed from the most unique 5' sequence as shown in FIGS. 1A and 1B and used either to inhibit transcription by preventing promoter binding to the upstream nontranslated sequence or translation of an human Reg Iγ-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A and 1B.

VIII. Expression Of Human Reg Iγ

Expression of the human Reg Iγ is accomplished by subcloning the cDNAs into appropriate vectors and transfecting the vectors into host cells. In this case, the cloning vector, pSport1, previously used for the generation of the cDNA library is used to express human Reg Iγ in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a polylinker containing a number of unique restriction sites.

Induction of an isolated, transfected bacterial strain with IPTG using standard methods produces a fusion protein which consists of the first seven residues of β-galactosidase, about 5 to 15 residues of linker, and the full length human Reg Iγ. The signal sequence provided by the vector directs the secretion of human Reg Iγ into the bacterial growth media which can be used directly in the following assay for activity. As the Reg Iγ gene contains sequences encoding a signal sequence, these gene sequences may be deleted from the Reg Iγ gene when the expression vector employed contains sequences encoding a signal sequence (alternatively, an expression vector which does not provide a signal sequence may be employed in conjunction with the full-length Reg Iγ gene).

In addition, the human Reg Iγ protein may be expressed as a fusion protein containing a histidine tag or GST tag using commercially available expression vectors [e.g., QIAExpress vectors (Qiagen) and pGex vectors (Pharmacia), respectively]. Suitable host cells and conditions for the induction/expression of the desired expression vectors are known to the art and available commercially. Histidine tagged human Reg Iγ may be purified from *E. coli* extracts using metal chelation chromatography using commercially available resins [e.g., Ni-NTA Agarose (Qiagen)]. GST-tagged human Reg Iγ may be purified from *E. coli* extracts using affinity chromatography using commercially available resins [e.g., glutathione-Sepharose beads (Pharmacia)]. Several other expression systems are available and may be employed to express fusion proteins comprising human Reg Iγ (e.g., pMAL vectors from New England Biolabs, Beverly, Mass.).

IX. Assay For Human Reg Iγ Activity

The ability of human Reg Iγ to induce cell growth can be demonstrated using pancreatic islets isolated from rat pancreas. Freshly isolated islets are prepared as described by Unno et al. [(1992) in Pancreatic Islet Cell Regeneration and Growth, Vinik, ed., Plenum Press, N.Y., pp. 61–69] and are exposed in in vitro culture to recombinant human Reg Iγ prepared as described above. The growth-promoting activity of human Reg Iγ can be demonstrated using methods well known to the art, including staining of untreated and treated islet samples to observe differences in cell division index. A higher cell cycle index indicates human Reg Iγ has induced cell growth. Alternatively, the treated and untreated islet samples may be cultured in the presence of radiolabeled thymidine to examine de novo DNA synthesis as described [Francis et al. (1992), supra]. An increase rate of DNA synthesis in the treated islets as compared to the untreated islets indicates human Reg Iγ has induced cell growth.

An extension of these assays can be used to compare the cell division indices of biopsied cell samples and observing the difference in cell division index. A higher cell cycle index indicates that human Reg Iγ has increased cell growth in the treated tissue. Alteratively, these assays may be employed to observe the therapeutic effect of administration of inhibitors of human Reg Iγ; inhibitors of human Reg Iγ would lower the cell cycle index in treated tissues.

Human Reg Iγ contains a number of amino acid residues which are conserved among the CRD of C-type lectins and therefore human Reg Iγ may bind carbohydrates. The ability of recombinant human Reg Iγ to bind carbohydrates may be demonstrated by examining the ability of human Reg Iγ to bind to affinity columns comprising carbohydrates (e.g., lactose, maltose, D-mannose, D-galactose, etc. which are available from Sigma Chemical Corp., St. Louis, Mo.) or by using the assay described by Christa et al. (1994), supra.

C-type lectins, including members of the reg/PSP gene family, are known to agglutinate bacteria. The ability of human Reg Iγ to agglutinate bacteria is demonstrated using the assay described by Iovanna et al. [(1991), supra]. Briefly, bacteria (e.g., *E. coli* strains KH802 or JM101) are grown at 37° C. to stationary phase in L-broth. The bacteria are then collected by centrifugation and washed in PBS. The washed bacteria are resuspended in PBS containing 0.5 mM $CaCl_2$ ($PBS/CaCl_2$) and are placed in the wells of microtiter plates at a concentration of approximately $5 \times 10^7$ bacteria/200 μl $PBS/CaCl_2$. Human Reg Iγ is then added at a variety of concentrations (e.g., 1 to 50 μg/ml) and the presence of macroscopic aggregation is monitored following a 3 hour incubation at 25° C. Concanavalin A and albumin at 50 μg/ml may be employed as positive and negative controls, respectively.

X. Production Of Human Reg Iγ Specific Antibodies

Human Reg Iγ substantially purified using polyacrylamide gel electrophoresis (PAGE) (Sambrook, supra) is used to immunize suitable animals (e.g., rabbits, hamsters, rats, mice, goats, sheep, etc.) and to produce antibodies using standard protocols (alternatively, recombinant human Reg Iγ fusion proteins may be purified by affinity or metal chelation chromatography and used to immunize animals). The amino acid sequence translated from human Reg Iγ is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel FM et al. (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel FM et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

Purified human Reg Iγ (native or fusion proteins) may be used to generate antibodies which react specifically with the human Reg Iγ protein. The production of both polyclonal and monoclonal antibodies utilize techniques standard to the art. Polyclonal antibodies contain a mixture of different types of antibodies that are specific for many different antigens present on the immunogen. Monoclonal antibodies contain a single species of antibody having a defined specificity.

Briefly, polyclonal antibodies are generated by immunization of a host animal with a purified protein. The serum of the immunized animal will contain antibodies directed against one or more epitopes of the injected protein. When rabbits are used for the production of polyclonal antibodies specific for human Reg Iγ, 50 to 1000 μg of purified human Reg Iγ is mixed with complete Freund's adjuvant and administered subcutaneously (s.c.) to the rabbit. Typically, multiple s.c. injections, each containing a maximum volume of about 400 μl are administered (up to 10 injections may be performed per animal). Alternatively, the immunogen may administered by intramuscular or intradermal injection. Four to six weeks following the initial or primary injection, secondary or booster injections are administered (these may utilize incomplete Freund's adjuvant). Additional boosts are given in 4–6 week intervals following the last injection. Immunized rabbits are bled (e.g., using the marginal ear vein) and the serum is screened for the presence of antibodies which react specifically with human Reg Iγ (e.g., by ELISA screening).

Immunization of mice is conducted as described above with the exception that the dose of antigen is 10–50 μg per injection (250 μl antigen solution mixed with 250 μl complete Freund's adjuvant) and injection is given intraperitoneally (i.p.). The first boost is given two weeks later and employs incomplete Freund's adjuvant; subsequent boosts are given at about 3 week intervals. Serum is collected from the immunized mice (e.g., by tail bleeding) and is screened for the presence of antibodies which react specifically with human Reg Iγ (e.g., by ELISA screening).

Monoclonal antibodies are produced by immunizing a host animal with purified human Reg Iγ protein (native or fusion). Once the host has produced antibodies specific for human Reg Iγ protein, the spleen of the host is removed. The plasma cells present in the spleen of the immune host are then fused with a myeloma cell (the "fusion partner") to produce hybridoma cells. When mice are immunized for the production of plasma cells to be used to generate hybridomas, suitable fusion partners include the X63Ag8.653, Sp2/0-Ag14, FO, NSI/1-Ag4-1, NSO/1 and FOX-NY cell lines [*Antibodies. A Laboratory Manual*, Harlow and Lane, Eds. (1988) Cold Spring Harbor Laboratory Press, Cold Spring Harbor, N.Y., p. 144]. When rats are immunized for the production of plasma cells to be used to generate hybridomas, suitable fusion partners include the YB2/0 and IR983F cell lines (Harlow and Lane, supra). Mice or rats are immunized as described above. Following the generation of specific anti-human Reg Iγ antibodies in the animals (typically following 2 to 3 booster injection and about 56 days following the initial injection), spleens are removed and splenocytes are fused (e.g., using polyethylene glycol) with the desired fusion partner. The fused cells are diluted in the appropriate selective medium and plated in multiwell culture plates. Each hybridoma cell produces a single type of antibody. Culture supernatant from individual hybridoma cells (removed from the hybridomas about 1 week following plating) is screened using standard techniques to identify those hybridoma cells expressing monoclonal antibodies reactive with human Reg Iγ (see Harlow and Lane, supra for a review of screening techniques).

When a fusion protein is utilized for the production of antibodies, the resulting antibodies may contain antibodies directed against the fusion partner (e.g., GST). These anti-fusion partner antibodies may be removed from a polyclonal sera by chromatography of the sera on a column containing the fusion partner immobilized to a solid support such as Sepharose beads (Pharmacia). For example, to remove anti-GST antibodies from a polyclonal sera raised against a GST fusion protein, the sera is chromatographed on a resin comprising the GST protein covalently linked to glutathione Sepharose. Anti-fusion partner antibodies may be excluded during the routine screening of hybridomas during the production of monoclonal antibodies.

XI. Purification Of Naturally Occurring Human Reg Iγ Using Specific Antibodies Naturally occurring or recombinant human Reg Iγ is substantially purified by immunoaffinity chromatography using antibodies specific for human Reg Iγ. An immunoaffinity column is constructed by covalently coupling human Reg Iγ antibody to an activated chromatographic resin such as CnBr-activated Sepharose (Pharmacia Biotech). After the coupling, the resin is blocked and washed according to the manufacturer's instructions.

Extracts from cells expressing human Reg Iγ are prepared by methods well known in the art (e.g., disruption of fresh or frozen ovarian or pancreatic tissue followed by centrifugation to remove cellular debris). Alternatively, a recombinant human Reg Iγ fragment containing an appropriate signal sequence (the native Reg Iγ or a heterologous signal sequence may be employed) may be secreted in useful quantity into the medium in which transfected cells are grown.

A human Reg Iγ-containing preparation is passed over the immunoaffinity column, and the column is washed under conditions that allow the preferential absorbance of human Reg Iγ (e.g., high ionic strength buffers in the presence of detergent). The column is eluted under conditions that disrupt antibody/human Reg Iγ binding (e.g., a buffer of pH 2–3 or a high concentration of a chaotrope such as urea or thiocyanate ion), and human Reg Iγ is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

We claim:

1. An isolated polynucleotide sequence of SEQ ID NO:2.

2. An isolated polynucleotide sequence of the complement of the polynucleotide sequence of claim 1.

3. An isolated polynucleotide sequence that hybridizes under stringent conditions to the nucleic acid sequence of SEQ ID NO:2.

4. A method for detecting the presence of the polynucleotide sequence of claim 3 in a biological sample containing nucleic acid, the method comprising the steps of:

(a) combining the biological sample with the polynucleotide sequence of claim 1 under conditions such that a hybridization complex is formed between the nucleic acid in the biological sample and the polynucleotide sequence; and (b) detecting the hybridization complex.

5. The method of claim 4, wherein the nucleic acid in the biological sample is ribonucleic acid.

6. The method of claim 5, wherein the detected hybridization complex correlates with expression of the polynucleotide sequence in the biological sample.

7. The method of claim 4, wherein the nucleic acid in the biological sample is deoxyribonucleic acid.

8. An antisense molecule consisting of the nucleic acid sequence complementary to the polynucleotide sequence of claim 1.

9. A pharmaceutical composition comprising the antisense molecule of claim 8 and a pharmaceutically acceptable excipient.

10. The polynucleotide sequence of claim 1, wherein polynucleotide sequence is contained in an expression vector.

11. The polynucleotide sequence of claim 10, wherein the expression vector containing the polynucleotide sequence is contained within a host cell.

* * * * *